US007201876B2

(12) United States Patent
Peper et al.

(10) Patent No.: US 7,201,876 B2
(45) Date of Patent: *Apr. 10, 2007

(54) ION-DETECTING SENSORS COMPRISING PLASTICIZER-FREE COPOLYMERS

(75) Inventors: Shane Peper, Los Alamos, NM (US); Yu Qin, Auburn, AL (US); Eric Bakker, Auburn, AL (US)

(73) Assignee: Auburn University, Auburn, AL (US)

( * ) Notice: Subject to any disclaimer, the term of this patent is extended or adjusted under 35 U.S.C. 154(b) by 349 days.

This patent is subject to a terminal disclaimer.

(21) Appl. No.: 10/384,097

(22) Filed: Mar. 7, 2003

(65) Prior Publication Data

US 2003/0213691 A1    Nov. 20, 2003

Related U.S. Application Data

(63) Continuation-in-part of application No. 10/313,090, filed on Dec. 5, 2002.

(60) Provisional application No. 60/417,866, filed on Oct. 11, 2002, provisional application No. 60/363,181, filed on Mar. 11, 2002.

(51) Int. Cl.
```
G01N 27/333    (2006.01)
G01N 21/01     (2006.01)
G01N 33/20     (2006.01)
C07C 69/00     (2006.01)
C07C 233/00    (2006.01)
```

(52) U.S. Cl. .................. 422/82.03; 204/416; 204/418; 205/781.5; 422/56; 422/82.01; 422/82.02; 422/82.05; 422/82.06; 422/82.07; 422/82.08; 422/82.09; 422/82.11; 436/73; 436/74; 436/79; 436/80; 436/81; 436/82; 436/83; 436/84; 436/149; 436/150; 436/151; 436/169; 436/172; 560/130; 560/138; 564/123; 564/152; 564/155; 564/192

(58) Field of Classification Search .................. 422/56, 422/82.01–82.03, 82.05–82.09, 82.11; 436/73–74, 436/79–84, 149–151, 169, 172; 205/781.5; 204/416, 418; 560/4, 130, 138, 205, 220–222; 564/123, 152, 155, 158–160, 192, 201
See application file for complete search history.

(56) References Cited

U.S. PATENT DOCUMENTS

| | | | |
|---|---|---|---|
| 4,162,282 A | | 7/1979 | Fulwyler et al. |
| 4,302,166 A | | 11/1981 | Fulwyler et al. |
| 4,463,032 A | * | 7/1984 | Arndt et al. ................ 427/222 |
| 4,507,425 A | * | 3/1985 | Weaver ...................... 524/460 |
| 5,198,301 A | * | 3/1993 | Hager et al. .......... 428/355 AK |
| 5,238,548 A | * | 8/1993 | van der Wal et al. ....... 204/418 |
| 5,260,195 A | * | 11/1993 | Azhar et al. .................... 435/25 |
| 5,644,069 A | * | 7/1997 | Liu et al. ...................... 73/23.2 |
| 5,747,349 A | | 5/1998 | van den Engh et al. |
| 6,143,558 A | | 11/2000 | Kopelman et al. |
| 6,143,570 A | * | 11/2000 | Alder et al. ................... 436/74 |
| 6,190,612 B1 | * | 2/2001 | Berger et al. ............ 422/82.07 |
| 6,254,831 B1 | * | 7/2001 | Barnard et al. .......... 422/82.08 |
| 6,277,330 B1 | * | 8/2001 | Liu et al. ................. 422/82.05 |
| 6,548,310 B1 | * | 4/2003 | Murata et al. ............... 436/518 |

FOREIGN PATENT DOCUMENTS

| | | | |
|---|---|---|---|
| EP | 0 432 990 A2 | | 6/1991 |
| EP | 0 490 631 A2 | | 6/1992 |
| JP | 57158202 | | 9/1982 |
| WO | 97/39337 | * | 10/1997 |
| WO | 00/54039 | * | 9/2000 |

OTHER PUBLICATIONS

Pretsch, E. et al, Helvetica Chimica Acta 1980, 63, 191-196.*
Harker, R. Chemistry in New Zealand 1990, 54, 59-60.*
Daunert, S. et al, Analytical Chemistry 1990, 62, 1428-1431.*
Bochenska, M. et al, Journal of Inclusion Phenomena and Molecular Recognition in Chemistry 1991, 10, 19-27.*
Xu, W. et al, Chinese Chemical Letters 1993, 4, 179-180.*
Xie, Z. et al, Journal of the American Chemical Society 1994, 116, 1907-1913.*
Cross, G. G. et al, Talanta 1994, 41, 1589-1596.*
King, B. T. et al, Journal of the American Chemical Society 1996, 118, 3313-3314.*
Xie, Z. et al, Inorganic Chemistry 1998, 37, 6444-6451.*
Smirnova, A. L. et al, Electroanalysis 1999, 11, 763-769.*
Heng, L. Y. et al, Analytical Chemistry 2000, 72, 42-51.*
Heng, L. Y. et al, Analytica Chimica Acta 2000, 403, 77-89.*
Heng, L. Y. et al, Electroanalysis 2000, 12 178-186.*
Heng, L. Y. et al, Electroanalysis 2000, 12, 187-193.*

(Continued)

*Primary Examiner*—Arlen Soderquist
(74) *Attorney, Agent, or Firm*—Hogan & Hartson LLP

(57) ABSTRACT

Ion-detecting sensors for detecting a target ion in a sample are provided. The sensor comprises a plasticizer-free copolymer comprised of polymerized units of methacrylate monomers having pendent alkyl groups of different length and a functionalized ionophore of said ion, wherein at least a portion of the functionalized ionophore is grafted into the copolymer through covalent linkages. Sensors may comprise ionophores such as hydrophilic crown ethers or functionalized derivative of 3-oxapentandiaminde-type ionophores. This invention further provides sensors for detecting target ions in a sample, comprising plasticizer-free molecularly imprinted polymers, wherein the polymers comprise polymerized units of methacrylate monomers having pendent alkyl groups of different length and a functionalized ionophore of said ion. In particular, a magnesium ion sensor comprising a functionalized derivative of a 3-oxapentandiaminde-type calcium ion-selective ionophore is provided. Sensors of this invention include carrier-based ion-selective electrodes or optodes such as thin film ion-specific optodes, particle-based optodes, or bulk optodes.

48 Claims, 9 Drawing Sheets

OTHER PUBLICATIONS

Malinowska, E. et al, Analytica Chimica Acta 2000, 421, 93-101.*
Tsang, C.-W. et al, Inorganic Chemistry 2000, 39, 3582-3589.*
Telting-Diaz, M. et al, Analytical Chemistry 2001, 73, 5582-5589.*
Peper, S. et al, Analytical Chemistry 2002, 74, 1327-1332.*
Qin, Y. et al, Analytical Chemistry 2003, 75, 3038-3045.*
Qin, Y. et al, Analytical Chemistry 2003, 75, 6002-6010.*
Bakker et al., "Plasticiser-Free Polymer Membrane Electrodes Containing a Methacrylic Copolymer Matrix" ELECTROANALYSIS, vol. 14, No. 19-20, 2002, pp. 1375-1381.

Rosatzin et al., "Preparation of Ca2+ Selective Sorbents by Molecular Imprinting Using Polymerisable Ionophores" Journal of Chemical Society, Perkin Transactions 2, No. 8, 1991, pp. 1261-1265.
Rosatzin et al., "Immobilization of Components in Polymer Membrane-Based Calcium-Selective Bulk Optodes," Analytical Checmistry, vol. 64, No. 18, 1992, pp. 2029-2035.
Schefer et al., "Neutral Carrier Based Ca2+ -Selective Electrode with Detection Limit in the Sub-Nanomolar Range," Analytical Chemistry, vol. 58, No. 11, Sep. 1986, pp. 2282-2285.

* cited by examiner

ION-DETECTING SENSORS COMPRISING PLASTICIZER-FREE COPOLYMERS

CROSS-REFERENCE TO RELATED APPLICATIONS

The present invention is a Continuation-in-Part application of U.S. Ser. No. 10/313,090, filed on Dec. 5, 2002, entitled "Plasticizer-Free Ion Detective Sensors." The present invention also claims priority to Provisional Application No. 60/363,181 filed on Mar. 11, 2002, entitled "Fixed Analyte-Ionophore Stoichiometry in Imprinted Polymers for Ion Sensors with Improved Selectivity," and Provisional Application No. 60/417,866, filed on Oct. 11, 2002, entitled "Halogenated dodecacarborane cation-exchangers for ion sensors.

GOVERNMENT INTERESTS

The invention was made in the course of work supported by grants GM59716 and GM58589 from the National Institutes of Health. The United States government has certain rights in this invention.

BACKGROUND OF THE INVENTION

1. Field of the Invention

The present invention is related to systems for detecting target ions in a sample, and more specifically, to ion sensors comprising an ionophore covalently anchored into a plasticizer free polymer. This invention is further related to imprinted plasticizer-free polymers for detecting target ions in a sample, comprising a novel ion-selective ionophore, and to sensors containing said imprinted polymers.

2. Description of the Prior Art

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

Carrier-based ion-selective electrodes (ISEs) and optical sensors (optodes) have been used for detecting target ions in body fluids for many years. ISEs produce a measurable electrical change upon contact with a fluid sample containing target ions. Optodes, thin film ion-specific optodes and particle-based optodes typically contain a target ionophore, i.e., a lipophilic complexing ligand capable of reversibly binding ions, and an indicator ionophore. The target ionophore complexes with the target ion when present, and the indicator ionophore provides an indication of such complexing, such as by a color change.

The selectivity of the sensor is related to the equilibrium constant of the exchange reaction of target and interfering ions between the organic and aqueous phases. It strongly depends on the ratio of complex formation constants and stoichiometry of these ions with the ionophore in the membrane phase (1). The stoichiometry between the ionophore and ions is a very important issue for designing ionophores and optimizing the response and selectivity of the sensor because the changes in the stoichiometric ratio can influence the selectivity of the ionophore dramatically. With the development of host-guest chemistry, a large number of ionophores for different inorganic and organic ions have been synthesized.

For example, the oxapentanediamide type calcium ionophore ETH 129 complexes with $Ca^{2+}$ with 3:1 stoichiometry and it also form $Mg^{2+}$ complex with 2:1 stoichiometry (2, 3). The structures of these two complexes have been reported (2). In the ETH 129-$Ca^{2+}$ complex, the nine oxygen atoms form a cavity with a radius of 102 pm, which is the ideal size for $Ca^{2+}$ (radius, 106 pm). On the other hand, the coordination of $Mg^{2+}$ is not optimized, therefore, ETH 129 has high calcium selectivity over magnesium ion and becomes one of the best ionophores for calcium ions. The high selectivity of ETH 129 based PVC-DOS and PVC-NPOE membrane has been reported by unbiased selectivity measurements (4).

Miniaturized optodes that function in accordance with bulk extraction principles have typically been either fiber optic or particle-based. Optical fiber-based optodes are usually fabricated by immobilizing a sensing layer on the distal end of an optical fiber by a simple dip-coating procedure. Sensors of this type have been developed for several clinical analytes, including $H^+$ (5), $Cl^-$ (6), $Na^+$ (7), and $K^+$ (8). Although this approach offers the advantages of reduced sample volume and high signal-to-noise ratio, it does not appear feasible for multiplexed analysis.

Particle-based optodes have been produced by several different approaches, such as heterogeneous polymerization techniques (9–10), solvent casting (11), and very recently with a high-throughput particle generator (12) (13). An obvious advantage of particle-based optodes is their ability to independently interrogate a sample and produce a distinguishable analytical signal. To date, particle-based optodes have been used for very innovative applications, including flow cytometry (13) and intracellular monitoring (9), (14). The lifetime of these sensors, however, still remains a concern. However, for particle-based probes used for intracellular measurements, lifetimes have been reported as short as 30 minutes (9), thus validating the need for methods that improve sensor lifetime.

Traditionally, poly(vinyl chloride) (PVC) has been the polymer matrix most commonly used in membrane-based ISEs and hydrophobic bulk optodes (15). This is primarily due to its high tensile strength, chemical inertness, and plasticizer compatibility (10).

There are several disadvantages, however, associated with the use of plasticized PVC in ion-selective sensors, one of which is plasticizer leaching (17). For example, it is known that exudation of plasticizer and leaching of dissolved ionophores may ultimately limit the lifetime of carrier-based sensors. The former process may lead to a decreased solubility of the active sensing components (18), and the latter a loss of selectivity. For in vivo applications, where biocompatibility is essential, it has been found that such component leaching induces a serious inflammatory response (19). Further, in recent years ionophore-based chemical sensing systems have started to be drastically miniaturized in size, and the leaching of components is a much more significant problem in these cases.

One approach addressing the issue of diffusion that has received a substantial amount of effort is the fabrication of plasticizer-free polymers. Several such polymers have been evaluated in ISEs or ion-selective field effect transistors (ISFETs), including polyurethanes (20), polysiloxanes (6), silicone rubber (21), (22), polythiophenes (23), epoxyacrylates (24), and methacrylic (25) and methacrylic-acrylic copolymers (26), (27). Polymers synthesized via free radical initiated mechanisms, such as methacrylic-acrylic copolymers, appear quite attractive because of the numerous polymerization methods and infinite monomer combinations available to create polymers with a diverse range of physical and mechanical properties (28). Hall et al. have reported a substantial amount of work in this area (27, 28, 29). Particularly, in PCT application WO 00/54039, Hall et al. describe a selective polymer material with an acrylate backbone and a plurality of pendant lipophilic plasticising groups. Acrylate monomers are used to synthesize the polymers. The polymers are self-plasticising and thus are plasticizer free.

U.S. patent application Ser. No. 10/313,090 describes a plasticizer-free ion-detecting sensor comprising a copolymer of methacrylate monomers with $R_1$ and $R_2$ pendant alkyl groups, and an ionophore for detecting the target ion, where $R_1$ is any of $C_{1-3}$ alkyl group and $R_2$ is any of $C_{4-12}$ alkyl group. The use of methacrylate monomers of different pendant alkyl groups allows one to achieve a polymer material with not only a plasticizer-free effect but also a better mechanical strength for a desired $T_g$. In addition, methacrylate polymers of the present invention are less sticky and therefore much easier to handle. Furthermore, the methacrylate monomers of the present invention have less of a characteristic smell, and thus are much easier to manufacture.

Another approach to improving detection limits by reducing ion diffusion efficiencies across ion-selective membranes has been to covalently immobilize the ionophores to the membrane. Puntener et al. have recently reported a lead-selective ionophore and a hydrogen ion-selective ionophore covalently attached onto a polyurethane polymer that was then blended with traditional PVC-DOS (30). While the resulting sensing characteristics were very promising, the PVC membrane matrix significantly reduced the ion selectivity (30). Therefore, there remains a need for improved polymer materials, especially with respect to sensors comprising immobilized ionophores.

Kimura has reported using the sol-gel technique for immobilizing ionophores onto polymer materials. While this method has been successfully for ion-selective electrode applications, it remains untested for optical sensing strategies (31). Alternatively, two other immobilization methods have been reported. One approach directly grafts the ionophore onto an existing polymer with active sites (32, 33), while another method blends two different polymers together, with one of them containing the grafted ionophore (34). While these approaches offer practical approaches for ionophore immobilization, they are quite cumbersome to perform and typically require the presence of a plasticizer.

Recently, two hydrophilic crown ether-type $K^+$-selective ionophores, 4-acryloylamidobenzo-15-crown-5 (AAB15C5) and 4'-acryloylamidobenzo-18-crown-6 (AAB18C6) (35), as well as a $Na^+$-selective ionophore, 4-tertbutylcalix[4]arene tetracetic acid tetraethyl ester (27), have reportedly been polymerized with other monomers by a simple one-step polymerization method. These polymers containing grafted ionophores showed comparable selectivity and improved lifetime when compared to ISEs with free, unbound ionophore present.

However, in contrast to $Na^+$ and $K^+$ ionophores, immobilization of $Ca^{2+}$ ionophores into an ion-selective electrode or optical sensor matrix has never been reported. Rosatzin has disclosed optical calcium sensors utilizing a covalently immobilized $H^+$-selective chromoionophore in addition to a freely dissolved calcium ionophore (36). Response times were shown to be prolonged by the addition of the immobilized chromoionophore, but other sensing characteristics were satisfactory. However, all calcium bulk optodes reported so far utilize calcium ionophores that form very strong complexes with calcium (37). The resulting optode response ranges are therefore not yet suitable for calcium determinations in physiological samples at neutral pH.

Molecular imprinting (MIP) is a technique used to create selective molecular recognition sites in highly stable synthetic polymers (38). In this technique a target molecule to be imprinted is combined with a mixture of functionalized and non-functionalized monomers to form a complex, and then the complex is polymerized with a cross-linker. After the polymerization is complete the template molecules are removed and the resulting polymer matrix contains imprinted binding sites or "cavities" which are the "negative" of the imprint molecule. These cavities have the memory of the binding properties and size of the template molecules so they can rebind with the target molecules in a sample with high selectivity.

Most imprinted polymers are based on acrylic and vinyl monomers. By far the most used systems are matrices based on methacrylate, methacrylamide and styrene.

Imprinted polymers are usually divided into three types, including small spherical particles with size below micrometer (microspheres), thin layers, and surface imprints (39). Microspheres can be prepared by emulsion polymerization (40) and by precipitation polymerization (41, 42). Precipitation polymerization is similar to bulk polymerization except for the larger volume of solvents, such that the imprinted particles precipitate instead of polymerizing together to form bulk polymer. This method avoids the steps of grinding and sieving, which can result in the loss binding sites in the polymers (42).

Imprinted polymers are especially useful for making sensors. Because molecular imprinting polymers are highly crosslinked, the most common form of these polymers is a powder, which makes them very suitable for solid state extraction, binding arrays, and preparation of a stationary phase in for chromatography.

Some MIP sensors use optical transducers such as fluorescence (39). However, MIP sensors based on electrochemical detection are more attractive in terms of the simplicity of the devices and predominance of the electrochemical biosensors in the market (43). Another type of electrochemical sensor is potentiometric sensor.

Rosatzin et al. (44) reported the preparation of calcium ions and magnesium ions imprinted polymer from N,N'-dimethyl-N,N'-bis(4-vinylphenyl)-3-oxapentanediamide, divinylbenzene and styrene, however, only the dissociation constant (K) in methanol-water was determined for the polymers. The imprinted polymers prepared against calcium ions and magnesium were found to bind calcium ions 6 and 1.7 times greater, respectively, compared to the blank polymer without templates.

Although molecular imprinting has wide applications in sensing, most analytes are neutral organic compounds, and ion sensors based on molecular imprinted polymers have received much less attention. Because ion sensing must be performed in solution, mass sensitive devices cannot be used.

Carrier-based ion-selective electrodes (ISEs) and optical sensors (optodes) may also include ion-exchangers for improving their ion selectivities. However, loss or ion-exchangers from optodes is crucial to their viability because they typically respond via coextraction or ion-exchange equilibria, whereby a decrease in the concentration of sites results in a decrease in sensor sensitivity. Ion-exchanger leaching may also soon play a role in dictating the lower detection limit of ISEs. Thus, the development of more robust alternatives to the tetraphenylborates that exhibit improved stability and lipophilicity is warranted.

Tetraphenylborate derivatives have been used as ion-exchangers in cation-selective solvent polymer membrane electrodes and bulk optodes for many years. In addition to reducing anion interference, tetraphenylborates also decrease membrane resistance (45), and improve ionophore selectivity by stabilizing the concentration of ion-ionophore complex (46). The delocalized monoanionic charge that these compounds possess, in combination with their sterically hindered molecular structure make them very weakly coordinating. This is a characteristic that leads to weak, non-specific ion pair formation and maximum ionophore-mediated selectivity of the membrane (47).

Because the unsubstituted tetraphenylborate (TPB⁻) is susceptible to decomposition via acid hydrolysis, oxidants, and light, the search for more chemically stable derivatives began many years ago (46), (45), (48). One successful derivative is the highly substituted 3,5[bis-(trifluoromethyl)phenyl]borate (NaTFPB) (47). Even though halogenated derivatives, such as NaTFPB, are more lipophilic and more resistant to phenyl cleavage, acid hydrolyzed decomposition still occurs albeit at a much slower rate (47), (49). This shortcoming limits the use of tetraphenylborates in systems requiring an acidic sample pH, as in the case of heavy metals, such as $Pb^{2+}$ (50).

Compounds that may be suitable alternatives to tetraphenylborates are carboranes, specifically closo-dodecacarboranes. These compounds possess many characteristics that may make them suitable ion-exchangers. Very weak ion pair formation is observed due to the lack of electron lone pairs and π-electrons, a property rarely found in anions (51). The desired lipophilicity of this class of carboranes can easily be tailored both at the boron vertices (48), (52–54) and at the carbon vertex (53), (54). The most lipophilic derivatives that have been synthesized are those of the perhalogenated (55) and peralkylated dodecacarborane anion (52).

U.S. patent application Ser. No. 10/313,090 describes the use of halogenated carboranes such as trimethylammonium-2, 3, 4, 5, 6, 7, 8, 9, 10, 11, 12 undecabromocarborane (TMAUBC) undecachlorinated (UCC), hexabrominated (HBC) and undecaiodinated (UIC) carborane anions as ion exchangers in ISEs and optodes.

In addition to potentially unparalleled lipophilicity, the carboranes possess many other characteristics that make them suitable for electrochemical applications. For example, they are not susceptible to acid and base hydrolysis and they are relatively inert to electrochemical oxidation (about 2.0 V vs. ferrocene/ferrocenium at Pt in dichloromethane) (51). High $I_h$ symmetry and tangentially delocalized σ-bonding make the carboranes one of the most chemically stable classes of compounds in chemistry. Furthermore, their bulky size (nearly 1 nm in diameter) and sufficient charge delocalization meet the criteria imposed for sufficient ion exchanging. Another advantage, important for bulk optode studies, is their lack of absorption in the UV-Vis spectrum.

SUMMARY OF THE INVENTION

One aspect of this invention is based on the discovery that copolymers of methacrylate monomers are suitable matrices for preparing plasticizer-free polymers comprising grafted ionophores, referred to as "graft polymers." The graft polymers of this invention can be used to prepare sensors such as ISE's and optodes for detecting target ions in a sample. In one embodiment, an ion-detecting sensor for detecting a target ion in a sample comprises (i) a plasticizer-free copolymer comprised of polymerized units of methacrylate monomers having pendent alkyl groups of different length; and (ii) a functionalized ionophore of said ion, wherein at least a portion of the functionalized ionophore is grafted into the copolymer through covalent linkages.

Preferably the methacrylate monomers comprise different pendent alkyl groups $R_1$ and $R_2$, wherein $R_1$ may be any of $C_{1-3}$ alkyl group, and $R_2$ may be any of $C_{4-12}$ alkyl group. In one embodiment, the plasticizer-free co-polymer is blended with poly(vinyl chloride) and a plasticizer.

Alternatively, the polymer includes monomer units in addition to methacrylate monomers, such as acrylate monomers.

Examples of functionalized ionophores include derivatives of 3-oxapentandiaminde-type calcium ionophore comprising a polymerizable moiety, and hydrophilic crown ether-type ionophores. In one embodiment, the ionophore is a novel 3-oxapentandiaminde derivative having the structure I:

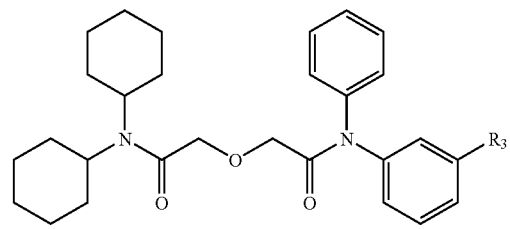

wherein $R_3$ is a polymerizable moiety such as an acrylic group.

The co-polymer matrices of the present invention may be in a form of membranes or particles.

The plasticizer-free ion-detecting sensors of the present invention may also include an indicator ionophore. The plasticizer-free ion-detecting sensor may further include an ion exchanger such as a halogenated carborane.

This invention further provides sensors for detecting target ions in a sample, comprising plasticizer-free molecularly imprinted polymers, wherein the polymers comprise polymerized units of methacrylate monomers having pendent alkyl groups of different length and a functionalized ionophore of said ion. In one embodiment, a plasticizer-free imprinted polymer of this invention is prepared by the method comprising:

(a) forming a complex between said ions and a functionalized ionophore;
(b) combining said complex with:
  (i) methacrylate monomers;
  (ii) a cross-linking monomer; and
  (iii) a polymerization initiator under conditions that allow said methacrylate monomers to copolymerize and said ionophore to become covalently bonded to said monomers to form a co-polymer containing said ionophore and said ions; and
(c) removing said ions from said polymer to provide said imprinted co-polymer.

According to one embodiment, the methacrylate monomers comprise $R_1$ or $R_2$ pendent alkyl groups, wherein $R_1$ is any of $C_{1-3}$ alkyl groups and $R_2$ is any of $C_{4-12}$ alkyl groups.

In particular, this invention provides a method of preparing a magnesium ion-selective imprinted polymer comprising a functionalized derivative of a 3-oxapentandiaminde-type calcium ion-selective ionophore is provided. In this embodiment, the functionalized ionophore is a compound having the structure I, wherein $R_3$ is an acrylic functional group, and the method comprises imprinting the polymer with magnesium ions.

The sensors of the present invention may be carrier-based ion-selective electrodes (ISEs) or optodes such as thin film ion-specific optodes, particle-based optodes, or bulk optodes. Ion-specific optodes include miniaturized sensing platforms such as sensing films immobilized on the end of optical fibers, self-referencing microspheres, and nanoscale intracellular probes.

This invention further provides a novel functionalized derivative of a traditional calcium ion-selective ionophore, said derivative having the structure I:

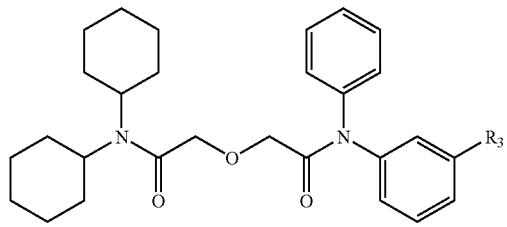

I wherein $R_3$ is a substituent comprising a polymerizable acrylic group.

Another aspect of the present invention provides an ion-detecting sensor comprising halogenated carboranes as ion-exchangers. In accordance with embodiment of the present invention, the ion exchangers may be trimethylammonium-2, 3, 4, 5, 6, 7, 8, 9, 10, 11, 12 undecabromocarborane (TMAUBC), and salts of undecachlorinatedcarborane (UCC), hexabrominatedcarborane (HBC) and undecaiodinatedcarborane (UIC) anions. In one embodiment, the ion-exchanger is trimethylammonium undecaiodinatedcarborane (TMAUIC).

DESCRIPTION OF THE FIGURES

The above-mentioned and other features of this invention and the manner of obtaining them will become more apparent, and will be best understood by reference to the following description, taken in conjunction with the accompanying drawings. These drawings depict only a typical embodiment of the invention and do not therefore limit its scope. They serve to add specificity and detail, in which.

DETAILED DESCRIPTION OF THE INVENTION

Figure 1:
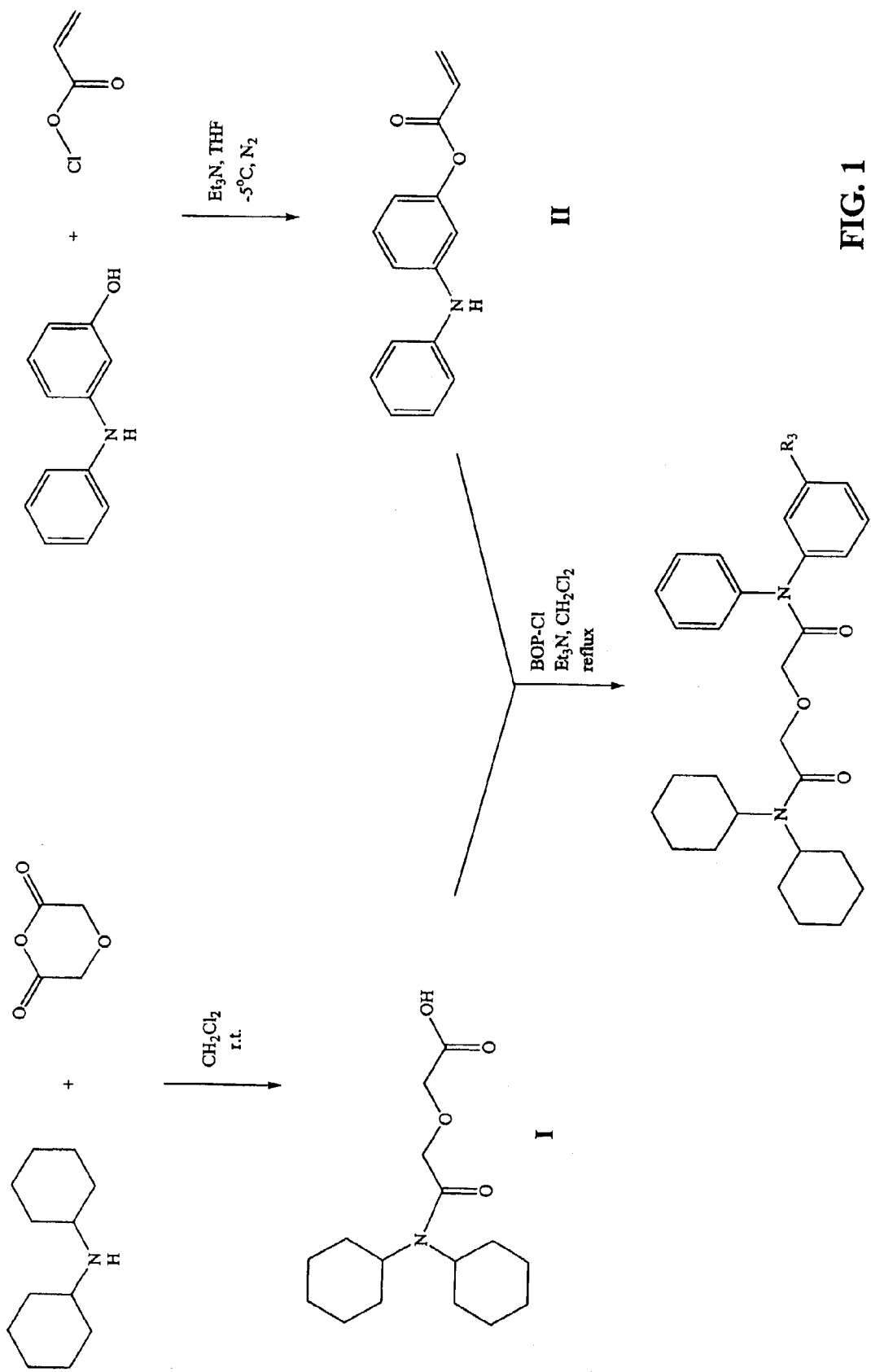
FIG. 1 shows the reaction scheme for the synthesis of AU-1.

One aspect of this invention is based on the discovery that copolymers of methacrylate monomers are suitable matrices for preparing plasticizer-free polymers comprising grafted ionophores, referred to as "graft polymers." The graft polymers of this invention can be used to prepare sensors such as ISE's and optodes for detecting target ions in a sample. In one embodiment, an ion-detecting sensor for detecting a target ion in a sample comprises (i) a plasticizer-free copolymer comprised of polymerized units of methacrylate monomers; and (ii) a functionalized ionophore of said ion, wherein at least a portion of the functionalized ionophore is grafted into the copolymer through covalent linkages.

It was further discovered that a plasticizer-free co-polymer of methacrylate monomers comprising a covalently grafted ionophore exhibits mechanical properties suitable for the fabrication of plasticizer-free ion-selective membrane electrodes and bulk optode films. In addition, the sensors were found to be suitable for the physiological assessment of ions at neutral pH.

Further, depending on the specific ionophore that is grafted into the copolymer, the plasticizer-free methacrylate copolymers of this invention demonstrate improved ion selectivity relative to similar methacrylate copolymers containing free (unbound) ionophores as well as conventional plasticized polymers containing the ionophore. Similarly, the plasticizer-free copolymer of this invention demonstrates improved response times relative to conventional plasticizer-containing polymers depending on the specific ionophore in the graft copolymer.

The ion-detecting sensors of this invention offer several advantages when compared to conventional sensors. For example, anchoring the ionophore to the polymer reduces diffusion of the ionophore across the polymer membrane relative to polymers containing unbound ionophores, which in turn improves the detection limit of the sensor. Further, the plasticizer-free polymer allows the assessment of a wide variety of ions without experiencing the deleterious effects resulting from plasticizer leaching.

The plasticizer-free copolymer matrix is a copolymer of methacrylate monomers with different pendant alkyl groups $R_1$ and $R_2$, wherein $R_1$ may be any of $C_{1-3}$ alkyl group, and $R_2$ may be any of $C_{4-12}$ alkyl group, as described in U.S. patent application Ser. No. 10/313,090, the content of which is specifically incorporated in its entirety herein by reference.

As used herein, the term "alkyl" refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl, ethyl, n-propyl, isopropyl, butyl, isobutyl, sec-butyl, tert-butyl, pentyl, isopentyl, tert-pentyl, hexyl, isohexyl, and the like.

In accordance with embodiments of the present invention, preferably $R_1$ is a $C_{1-2}$ alkyl group, and $R_2$ is a $C_{8-12}$ alkyl group. In one embodiment, methyl methacrylate and decyl methacrylate monomers are used for forming a methyl methacrylate-decyl methacrylate (MMA-DMA) copolymer matrix of the present invention. Methacrylate monomers of the present invention are commercially available from, for example, Polysciences, Inc. (Warrington, Pa.). Alternatively, the methacrylate monomers can be prepared by standard methods known in the art or via thermally initiated free radical solution polymerization as described in copending U.S. patent application Ser. No. 10/313,090, which is incorporated herein by reference.

The copolymers of the present invention comprising a covalently grafted ionophore may be used in connection with a wide variety of ionophores for detecting different target ions, provided that the ionophore contains a functional group that allows it to be covalently grafted or anchored to a polymer matrix. The functional is required to allow the ionophore to react with a reactive group of the copolymer, such as a carbon-carbon double bond, so as to form covalent linkages, whereby the ionophore becomes covalently grafted onto the copolymer.

In one embodiment, the ionophore comprises a polymerizable group, and the ionophore is covalently grafted onto a plasticizer-free matrix by copolymerizing the ionophore with methacrylate monomers such as MMA and DMA monomers. In this embodiment, the copolymer may comprise a random distribution of immobilized ionophore within the MMA-DMA polymer chain.

The terms "polymer" and "copolymer" are used interchangeably and refer to a chemical compound or mixture of compounds formed by polymerization and comprising repeating monomer units, wherein the polymer can comprise one type of monomer unit or can contain two or more different monomer units.

The terms "covalently grafted ionophore," "covalently anchored ionophore," and "covalently immobilized ionophore" are used interchangeably herein and refer to an ionophore that is attached to a polymer through covalent bonds.

The terms "functionalized ionophore" refers to an ionophore having a reactive functional group through which allows the ionophore to become covalently bonded to a copolymer. Examples of such functional groups include, but are not limited to, carbon-carbon double bonds such as acrylic and methacrylic groups, carbon-carbon triple bonds, and carbonyl groups. A "polymerizable ionophore" is a functionalized ionophore comprising a polymerizable functional group.

Examples of functionalized ionophores suitable for purposes of this invention include hydrophilic crown ether-type ionophores, such as 4'-acryloylamidobenzo-15-crown-5 and 4'-acryloylamidobenzo-18-crown-6. Hydrophilic crown ethers of the type described herein are well known in the art and are commercially available or may be prepared using conventional synthetic techniques.

When ISE sensors of this invention were prepared with graft copolymers comprising hydrophilic crown ethers immobilized onto MMA-DMA copolymers, the sensors showed increased response times and improved ion selectivities relative to MMA-DMA copolymers containing free (unbound) hydrophilic crown ethers. In addition, these ISE sensors demonstrated superior ion selectivity to that reported for ISE sensors comprising conventional PVC membranes containing a plasticizer such as NPOE.

Other example of functionalized ionophores suitable for this invention include functionalized derivative of a 3-oxapentandiaminde-type calcium ion-selective ionophore, said derivative having the structure I:

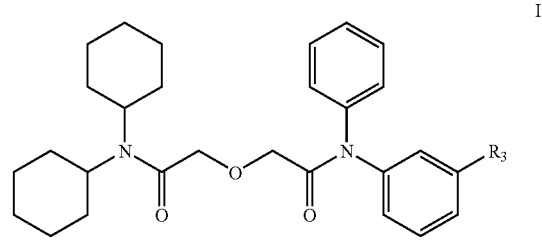

where $R_3$ is a substituent comprising an unsaturated group. In one embodiment, $R_3$ is a polymerizable acrylic group —O(C=O)CH=CH$_2$, and this compound is referred to herein as AU-1. Compound AU-1 may be prepared according to the method described in Example 1. The AU-1 ionophore may be grafted into any suitable matrix. In one embodiment, the matrix is a plasticizer-free matrix comprising a co-polymer of methacrylate monomers having $R_1$ or $R_2$ pendant alkyl groups, wherein $R_1$ is any of $C_{1-3}$ alkyl groups and $R_2$ is any of $C_{4-12}$ alkyl groups. This invention introduces the first calcium ionophore covalently anchored onto a hydrophobic polymer matrix for use in ion-selective electrode and optode applications.

Accordingly, this invention further provides a novel ionophore comprising compound I, where $R_3$ is —O(C=O)CH=CH$_2$.

For example, when ISE sensors were prepared with graft copolymers comprising MMA-DMA-AU-1 graft copolymers (i.e., AU-1 covalently grafted into a MMA-DMA copolymer matrix), the sensors exhibited excellent response times (e.g., approximately 2 minutes) relative to MMA-DMA copolymers containing free AU-1. In addition, sensors containing MMA-DMA-AU-1 graft copolymers exhibited a Nernstian response towards calcium ions with selectivity over sodium, potassium, and magnesium ions that was comparable to electrodes containing free AU-1 dissolved in a MMA-DMA copolymer matrix.

Sensors containing MMA-DMA-AU-1 also exhibited mechanical properties suitable for the fabrication of plasticizer-free ion-selective membrane electrodes and bulk optode films by solvent casting and spin coating techniques.

Plasticizer-free copolymers of the present invention comprising a covalently grafted ionophore may be made in accordance with methods known in the art or the methods described herein. For example, in one embodiment the graft copolymer is prepared by thermally initiated free radical solution polymerization of a mixture of methacrylate monomers and a functionalized ionophore as described herein in detail in Example 2.

Alternatively, other methods known in the art may be used to covalently graft the ionophore to the matrix. For example, a sol-gel technique may be used to prepare the graft copolymer. Another approach involves directly grafting the ionophore onto an existing polymer with active sites. Yet another approach involves blending two different polymers together, with one of them containing the grafted ionophore. Alternatively, a solution containing methacrylated monomers and the functionalized ionophore can be irradiated with an electron beam to cause polymerization and covalent attachment of the functionalized ionophore onto the methacrylate copolymer.

The amount of each monomeric subunit needed to produce copolymers with a desired glass transition temperature $T_g$ for optimal mechanical strength may be calculated using the Fox equation (56). The $T_g$ is typically determined experimentally with a differential scanning calorimeter, a standard instrument for this purpose. Polymers with very low $T_g$ values are normally much softer and more difficult to handle mechanically. In accordance with embodiments of the present invention, a copolymer of the present invention has a glass transitional temperature ($T_g$) of about or less than 0° C.

A sufficient amount of functionalized ionophore is combined with the copolymer to obtain the desired improvement in desired properties of the copolymer, such as ion selectivity and response time. Such properties may be quantitatively measured by well-known test methods. For example, a sandwich assay can be used to assess the binding constant of the bound ionophore to the ion and to study the diffusion constant of the ionophore as described in Example 4.

The precise minimum amount of functionalized ionophore required to produce a significant enhancement of such properties will, of course, vary depending upon the chemical compositions, structures, and molecular weights of the components employed as well as the extent of grafting achieved. In general, however, it will be advantageous to use at least one part by weight of the functionalized ionophore for every 100 parts by weight of the copolymer.

When the functionalized ionophore is a hydrophilic crown ether, the ionophore is added in an amount between about 1–2% by weight. When the functionalized ionophore is AU-1, the ionophore is added in an amount between about 1% and 5% by weight, with 5% being preferred.

The conditions necessary to achieve at least partial grafting of the components of the polymer composition will vary depending upon the reactivities of the individual components. For example, when the ionophore comprises an acrylic functional group (as with ionophore AU-1) which can react with the methacrylate monomer unit of the copolymer, then the grafting conditions may comprise a thermal or photoinitiated co-polymerization in an organic solvent such as benzene. When AU-1 was grafted onto a MMA-DMA, the amount of AU-1 that polymerized with the MMA and DMA monomers was measured to be about 92%.

In one embodiment, the plasticizer-free graft copolymers of this invention may be blended, admixed, or combined with other polymers to obtain blends having improved properties or performance characteristics. For example, the polymer composition when blended with poly(vinyl chloride) and a plasticizer has the beneficial effect of increasing the response time of the graft polymer. The relative proportion of PVC polymer:graft polymer composition may be varied as desired, preferably from about 90:10 to 80:20 on a weight basis.

This invention further provides sensors for detecting target ions in a sample, comprising plasticizer-free molecularly imprinted polymers. In one embodiment, a plasticizer-free molecularly imprinted polymer of this invention is prepared by precipitation polymerization to produce the imprinted polymer as microparticles. According to this method, a complex is prepared by combining the target ion with a functionalized ionophore. This complex is then combined with methacrylate monomers, a cross-linking monomer, and a polymerization initiator under suitable polymerization conditions. The monomers polymerize, thereby "encasing" the ions within the copolymer. The copolymer is formed as microparticles, which are collected by any suitable method such as centrifugation. The ions are then removed from the microparticles, and the resulting material contains imprinted binding sites which are the "negative" of the imprint ion.

The MIP polymer may also be in a form of membrane. The membrane can be formed by well-known methods in the art or as described in Example 7.

In accordance with embodiments of the present invention, the methacrylate monomers comprise different pendant alkyl groups $R_1$ and $R_2$, wherein $R_1$ may be any of $C_{1-3}$ alkyl group, and $R_2$ may be any of $C_{4-12}$ alkyl group. In one embodiment, methyl methacrylate and decyl methacrylate monomers are combined with the ionophore/ion complex to form an imprinted polymer matrix of the present invention.

The functionalized ionophore is preferably a derivative of a 3-oxapentandiaminde-type a compound having the structure I.

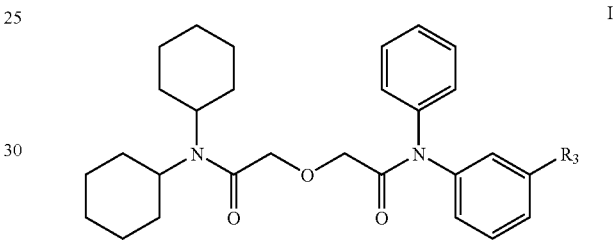

where $R_3$ is a substituent comprising a polymerizable group. In one embodiment, compound I is AU-1, where $R_3$ is polymerizable acrylic group $—O(C=O)CH=CH_2$. In this embodiment, the ionophore co-polymerizes with the methacrylate monomers such that the ionophore is imbedded in the polymer matrix.

The prior art describes unsuccessful attempts to make magnesium ion selective polymer membranes comprising 3-oxapentandiaminde-type ionophores by imprinting such polymers with magnesium ions (44). However, the present inventors unexpectedly discovered that when a polymer comprising the novel functionalized ionophore AU-1 of this invention was imprinted with magnesium ions, the polymer showed high selectivity for magnesium ions as discussed below in detail. This invention therefore demonstrates the first magnesium ion sensor prepared with a derivative of a traditional calcium ion-selective ionophore. In particular, this invention provides a method of preparing a magnesium ion-selective imprinted polymer comprising the novel functionalized ionophore having the structure I wherein $R_3$ is an acrylic functional group, wherein the method comprises imprinting the polymer with magnesium ions.

Any suitable cross-linkers known in the art may be used for the preparation of imprinted copolymers of this invention. Examples of cross-linkers include, but are not limited to, ethylene glycol dimethacrylate and divinyl benzene.

It was discovered that the amount of cross-linker is very important for preparing selective imprinted polymers. That is, it was observed that the smaller the ratio of ions to cross-linker, the higher the selectivity of the imprinted copolymer. For example, when the cross-linker was ethylene glycol dimethacrylate, the selectivity of the polymer was observed to increase sharply at about 40% by volume of cross-linker and became stable at 60% by volume of cross-linker. Thus, the stoichiometry of the cross-linker and imprint ion can be varied to alter the selectivity of the imprinted copolymer.

The graft polymers and imprinted polymers of the present invention may be used to fabricate plasticizer-free ion-selective membranes or particles for a variety of sensors including, but not limited to, carrier-based ion-selective electrodes (ISEs), thin film ion-specific optodes, particle-based optodes, and bulk optodes, ultraminiaturized ion-specific probes and nanoscale intracellular probes, and low detection limit sensors. Examples of ultraminiaturized ion-specific probes sensing films immobilized on the end of optical fibers, self-referencing microspheres. For example, a graft polymer or an imprinted polymer of this invention may be used to fabricate polymer membranes of an ISE in accordance with methods described in Examples 3 and 7 of the present invention or any other methods known to one skilled in the art. Polymers of this invention may also be used to fabricate thin films to be used in a thin film ion-specific optode or to fabricate microsphere particles to be used in particle-based optodes in accordance with methods known in the art. For example, the electrodes and optodes may be prepared, for example, by solvent casting and spin coating techniques.

When the plasticizer-free ion-detecting sensor of the present invention is in a form of optodes, the sensor further includes an indicator ionophore. Examples of indicator ionophores include, but are not limited to, a pH indicating chromoionophore, a chromoionophore, a fluoroionophore, a pH indicator, or a pH indicating fluoroionophore.

The ion-detecting sensors of the present invention may also include other additives such as ion-exchangers to enhance the extraction of the target ion from the aqueous sample and the migration of the target ion into the polymer matrix.

While any ion exchangers that provide lipophilic anionic sites on the polymer matrix may be used, preferably, carba-closo-dodecaborates, particularly halogenated carborane anions, are used as ion exchangers.

Examples of halogenated dodecacarborane cation exchangers suitable for purposes of this invention include, but are not limited to, trimethylammonium-2, 3, 4, 5, 6, 7, 8, 9, 10, 11, 12 undecabromocarborane (TMAUBC) (U.S. patent application Ser. No. 10/313,090), and salts (e.g., trimethylammonium salts) of undecachlorinatedcarborane (UCC), hexabrominatedcarborane (HBC) and undecaiodinatedcarborane (UIC) anions. Demonstrating excellent stability and suitable electrostatic properties, these halogenated carboranes UIC in particular, are a very promising alternative to the tetraphenylborates and should find widespread application in the field of chemical sensors.

The term "carba-closo-dodecacarborane" refers to a closed carborane cage comprised of 11 boron atoms and one carbon atom.

The term "halogenated dodecacarborane" refers to a carborane derivative wherein one or more hydrogen atoms are replaced by a halogen atom.

The term "undecahalogenated carborane anion" refers to a carborane derivative wherein all 11 boron hydrogens have been replaced by halogen atoms.

The ion-detecting sensors of the present invention may be used for detecting ions of all types of body fluid samples. Examples of the samples include, but are not limited to, whole blood, spinal fluid, blood serum, urine, saliva, semen, tears, etc. The fluid sample can be assayed neat or after dilution or treatment with a buffer.

Additional features and advantages of this invention shall be set forth in part in the description that follows, and in part will become apparent to those skilled in the art upon examination of the following specification or may be learned by the practice of the invention. The advantages and novel features of this invention may be realized and attained by means of the instrumentalities, combinations, and methods particularly pointed out in the appended claims.

EXAMPLE 1

Syntheses of N,N-dicyclohexyl-N'-phenyl-N'-(4-acrylophenyl)-3-oxapentanediamide (AU-1)

Reagents: Dicyclohexylamine, diglycolic anhydride, 3-hydroxy diphenylamine, acryloyl chloride, triethylamine and bis (2-oxo-3-oxazolidinyl)-phosphinic chloride (BOP-Cl) were reagent grade from Aldrich (Milwaukee, Wis.). All solvents used for syntheses were obtained from Fisher Scientific (Pittsburgh, Pa.) and dried before using.

The monomers methyl methacrylate, 99.5% and n-decyl methacrylate, 99% were obtained from Polysciences, Inc. (Warrington, Pa.). 4'-acryloylamidobenzo-15-crown-5 (AAB15C5) and 4'-acryloylamidobenzo-18-crown-6 (AAB18C6) were obtained from Acros Organics (Pittsburgh, Pa.). The polymerization initiator 2,2'-azobis-isobutyronitrile, 98%, (AIBN) was obtained from Aldrich. Benzene, dichloromethane and 1,4-dioxane were reagent grade and obtained from Fisher. Benzene and dichloromethane were purified by fractional distillation after refluxing with calcium hydride for 4 hours. Inhibitors were removed from the monomers by washing with a caustic solution containing 5% (w/v) NaOH and 20% NaCl in a 1:5 (monomercaustic solution) ratio and water. The organic phase was separated and dried with anhydrous $Na_2SO_4$. This purification process has previously been reported (28). AIBN was recrystallized from warm methanol prior to use. N,N,N',N'-tetracyclohexyl-3-oxapentanediamide (ETH 129), 9-(diethylamino)-5-octadecanoylimino-5H-benzo[a]phenoxazine (chromoionophore I, ETH 5294, sodium tetrakis [3,5-bis (trifluoromethyl)phenyl]borate (NaTFPB), o-nitrophenyloctylether (NPOE), bis(2-ethylhexyl)sebacate (DOS), high molecular weight poly(vinyl chloride), tetrahydrofuran (THF) and all salts were purchased in Selectophore or puriss quality from Fluka (Milwaukee, Wis.). Aqueous solutions were prepared by dissolving the appropriate chloride salts in Nanopure purified water (18 MΩ cm).

Syntheses: FIG. 1 shows a reaction scheme for the synthesis of AU-1, which was prepared as follows.

Step one: To a stirred solution of diglycolic anhydride (1.16 g, 10 mmol) in 100 mL dry dichloromethane was added dicyclohexylamine (3.62 g, 20 mmol). The mixture was stirred at room temperature for 3 hours. Then, 20 mL of 6 N HCl was added to the reaction mixture. The solid was filtered and the organic layer of the filtrate was separated and dried with anhydrous sodium sulfate. Dichloromethane was removed using a rotary evaporator. White crystals of 3-oxapentane acid-N,N'-dicyclohexylamide (I) were recrystallized from ethyl acetate in 92% yield (2.74 g).

Step two: 3-hydroxyl diphenylamine (3.33 g, 18 mmol) was dissolved in 25 mL of dry THF under $N_2$. Subsequently, triethylamine (1.98 g, 19.5 mmol) was added to the solution. Afterwards, acryloyl chloride (1.62 g, 18 mmol) was added dropwise to the reaction mixture with a syringe under $N_2$ at −5° C. After 25 min, 30 mL of a saturated $NaHCO_3$ solution was added to quench the reaction. The organic phase was then separated and washed with water. After evaporation of the solvent, the crude product was purified by flash chromatography (1:1 EtOAc/Hexane). A pale yellow solid, 3-acrylate-diphenylamine (II) was obtained in 60% yield (2.88 g).

Step three: To a solution of I (0.736 g) and II (0.529 g) in 30 mL of dry $CH_2Cl_2$ was added $Et_3N$ (0.8 g) at room temperature while stirring. Then, 0.612 g of BOP-Cl was added. The mixture was refluxed for 24 h. The reaction mixture was washed with 10 mL of saturated $NaHCO_3$ and 10 mL water. The organic phase was obtained after separation and evaporation of the solvent. The leftover was purified using flash chromatography (1:5 EtOAc:Hexane). A pale yellow solid ($C_{31}H_{38}N_2O_5$ MW: 518.65) was obtained in 50% yield. The final product (AU-1) was characterized by $^1$HNMR: $\delta_H$ (250 MHz; $CDCl_3$) 1.80–1.04 (m, IS H), 2.38 (m, 2H), 2.92 (m, 1H), 3.43 (m, 1H), 4.15 (s, 2H), 4.27 (s, 2H), 3.99 (dd, 1H), 6.27 (dd, 1H), 6.58 (dd, 1H), 7.50–7.07 (m, 9H). $^{13}$CNMR: (250 MHz; $CDCl_3$) 25.5, 26.0, 26.8, 30.1, 31.5, 56.2, 57.1, 69.4, 71.3, 120.4, 122.0, 123.9, 124.0, 128.0, 130.0, 133.1, 141.0, 141.1, 142.8, 151.2, 164.3, 168.1, 169.4. EIMS analysis: m/z 518 ($M^+$, 5%), 252 (30), 185 (27), 280 (100).

EXAMPLE 2

Synthesis of Polymers Containing AU-1

All polymers were synthesized via thermally initiated free radical solution polymerization. The amount of methyl methacrylate and n-decyl methacrylate used was the same as reported previously (19). For polymers containing grafted $K^+$-selective ionophores, 1 wt % AAB15C5 and AAB18C6 were used. The amount of AU-1 varied from 1 wt % to 5 wt %. The calculated amounts (according to the Fox equation (56)) of each monomeric unit were added to 5 mL of dry benzene. The solution was purged with $N_2$ for 10 minutes before adding AIBN, 3.4 mg for grafted potassium ionophore polymers and 5.1 mg for polymer with AU-1. The homogeneous solution was continuously stirred and the temperature was ramped to 90° C., which was maintained for 16 hours. After the reaction was complete, the solvent was evaporated and the polymer was redissolved in 10 mL of dioxane. Aliquots of polymer solution (2 mL) were added to 100 mL of distilled water under vigorous stirring. The white precipitate was collected and dissolved in 25 mL of dichloromethane, followed by water removal with anhydrous $Na_2SO_4$ and filtering. The solvent was evaporated and the resultant transparent polymer was dried under ambient laboratory conditions.

EXAMPLE 3

Preparation of ISE Membrane and Optode Thin Films Comprising Graft Polymers

ISE membranes were prepared by dissolving NaTFPB (5 mmol/kg), ionophore (20 mmol/kg, if used), PVC, and plasticizer (DOS or NPOE) to give a total cocktail mass of 140 mg in 1.5 mL of THF. For the plasticizer-free membrane with free calcium ionophore AU-1 the cocktail contained ionophore, NaTFPB and blank MMA-DMA polymer were used, while the cocktail of the membrane with grafted ionophore contained 5 mmol/kg NaTFPB and either MMA-DMA-AU-1, MMA-DMA-AAB 15C5 or MMA-DMA-AAB 18C6 copolymer.

Cocktails were poured into glass rings 2.2 cm i.d.) affixed onto glass microscope slides. The solvent was evaporated overnight to give a transparent membrane. The plasticizer-free MMA-DMA membrane was soaked in water for an hour and carefully peeled from the glass slide with a scalpel. The parent membranes were then conditioned overnight in 0.01 M $MgCl_2$. Discs (6 mm in diameter) were cut from the parent membranes and mounted into Philips electrode bodies (IS-561, Glasbtaserei Moller, Zurich, Switzerland). 0.01 M $MgCl_2$ was used as the inner filling solution. The electrodes were titrated with different sample solutions. All of the experimental results are the average of at least three electrodes, with calculated standard deviations.

EXAMPLE 4

Measurement of Stability Constants of Graft Polymers

The sandwich technique was used to measure the stability constant of the free AU-1 in different matrices. One single parent membrane contained 20 mmol/kg ionophore and 5 mmol/kg NaTFPB in PVC-DOS, PVC-NPOE or MMA-DMA polymer while the other segment contained only NaTFPB in the same matrix. For the immobilized ionophore one single membrane contained 1.5 mmol/kg NaTFPB and 10 wt % MMA-DMA-AU-1 polymer in PVC-DOS or blank MMA-DMA while the other one contained the same amount of NaTFPB in PVC-DOS or blank MMA-DMA polymer. The parent membranes were conditioned in 0.01 M $CaCl_2$ overnight. The sandwich membrane method was used as reported (59, 58). All membrane electrode potential measurements were performed at laboratory ambient temperature in unstirred salt solutions (identical to the conditioning and inner filling solution) versus a Ag/AgCl reference electrode with a 1 M LiOAc bridge electrolyte.

For the three-component thin-film-based optode, a total of 300 mg of membrane components containing 6.0 mmol/kg ETH 5294, 15 mmol/kg NaTFPB and polymer were dissolved in 1.75 mL of THF. A 200-µL aliquot of the cocktail was transferred with a syringe onto a quartz disk placed in a spin-coating device (59). The 2–3 µm-thick films were equilibrated in different solutions and characterized by fluorescence microscopy and spectroscopy as previously reported (11, 12). All the data points are the average of five measurements, with calculated standard deviations.

For the three-component thin-film-based plasticizer free optode, a total of 300 mg of membrane components containing 5.5 mmol/kg ETH 5294, 16.5 mmol/kg NaTFPB and MMA-DMA-AU-1 polymer (containing 90 mmol/kg ionophore) were dissolved in 1.75 mL of THF. An alternate composition contained 1 mmol/kg ETH 5294, 3 mmol/kg NaTFPB, 10 wt % MMA-DMA-AU-1, PVC and DOS (1:2), with the same total mass. The films were prepared with the same procedure as described above.

EXAMPLE 5

Preparation of Imprinted Polymers

Reagents: The monomers methyl methacrylate (MMA), 99.5%, ethylene glycol dimethacrylate (EGDMA), 98%, the polymerization initiator 2,2'-azobisisobutyronitrile, 98%, (AIBN) and anhydrous acetonitrile was obtained from Aldrich (Milwaukee, Wis.). Inhibitors were removed from the monomers by distillation. AIBN was recrystallized from warm methanol prior to use. N,N,N',N'-tetracyclohexyl-3- oxapentanediamide (ETH 129), sodium tetrakis [3, 5-bis (trifluoromethyl)phenyl]borate (NaTFPB), o-nitrophenyloctylether (NPOE), bis(2-ethylhexyl)sebacate (DOS), high molecular weight poly(vinyl chloride), tetrahydrofuran (THF) and all salts were purchased in Selectophore or puriss quality from Ruka (Milwaukee, Wis.). Aqueous solutions were prepared by dissolving the appropriate chloride salts in Nanopure purified water (18 MΩ cm). AU-1 was synthesized as reported by Qin et al. and as shown in FIG. 1 (58).

Synthesis of imprinted polymers: First, the complexes of the functional ionophore with ions (templates) were prepared. Anhydrous $CaCl_2$ or $MgCl_2$ was added to a solution of AU-1 in chloroform in a mole ratio of 1:3 or 1:2 (ion to ionophore), respectively. The solutions were stirred for 24 hours at room temperature. The salts dissolved upon complex formation between the ionophore and the ions. The solvent was evaporated under reduced pressure to provide the complex as a pale yellow solid.

To prepare the imprinted polymers, the complex was mixed with methyl methacrylate and crosslinker EGDMA in acetonitrile in glass bottle according to the formulations in Table 5. The solution was purged with $N_2$ for 20 min and initiator AIBN was added. The bottle was then sealed and put in a water bath at 65° C. for 24 hours. White polymer microspheres were removed from the solution by centrifugation. The ions were extracted by washing with methanol containing 5% acetic acid (12 hours) and methanol (8 hours). The polymers were then dried in vacuo.

EXAMPLE 6

Pulse Voltammetry Experiments of Membranes Comprising ETH 129

Ion-selective membranes containing the ionophore ETH 129 were prepared first by pouring a cocktail of the membrane components in a glass ring fixed onto a glass slide. The membrane cocktail contains 10 mmol/kg ETH 129, 10 wt % of the inert lipophilic salt ETH 500, PVC and NPOE (1:2 by weight) in 1.5 mL THF. A 200 μm thick membrane is obtained after THF is evaporated. A 6 mm diameter membrane is cut from the parent membrane and mounted in a Philips body electrode. The inner electrolyte for the ion-selective electrode was 0.1 M KCl with a Ag/AgCl internal contact. The electrodes were conditioned in a solution identical to the inner filling solution overnight before measurement. All membrane electrode potential measurements were performed at laboratory ambient temperature. The ion-selective electrode served as the working electrode and a Ag/AgCl electrode as the counter electrode.

Normal pulse voltammetry data was obtained by increasing the voltage pulsed from +1.0 V up to −1.0 V. The uptake potentials were applied for 1 second, while the stripping potential was held for 10 seconds.

EXAMPLE 7

Preparation and Measurement of ISE Membranes Containing Imprinted Polymers

ISE membranes were prepared by mixing the polymer powder prepared as described in Example 5 (80% w/w) and PVC (20% w/w) in THF. The mixture was stirred on the shaker for 20 min and the suspension was loaded onto the top of the PVC tubing. THF was evaporated for 24 hours. The thick layer (1 mm) obtained contains about 12 mg polymer. The electrodes were then conditioned in 0.01 M NaCl solution overnight. The electrodes were titrated with different sample solutions by using unbiased selectivity measurement (4). All of the experimental results are the average of at least three electrodes, with calculated standard deviations.

Synthesis of the undecahalogenated carborane trimethylammonium salts, [Me3NH][1-H—CB11X11] (where X=Cl, Br, and I), as described in Examples 8–11 were performed according to the procedure described by Xie et. al. (60).

EXAMPLE 8

Synthesis of [Me$_3$NH][1-H—CB$_{11}$Cl$_{11}$] (UCC)

Reagents: For membrane preparation, high molecular weight poly(vinyl chloride), bis(2-ethylhexyl sebacate) (DOS), 2-nitrophenyl octyl ether (NPOE), tert-butylcalix[4]arene-tetrakis(N,N-dimethylthioacetamide) (Lead Ionophore IV), sodium tetrakis[3,5-bis(trifluoromethyl)phenyl] borate (NaTFPB), and tetrahydrofuran (THF) were of Selectophore quality from Fluka (Milwaukee, Wis.). Cesium carborane ($CsCB_{11}H_{12}$) and silver 7, 8, 9, 10, 11, 12-hexabromocarborane ($AgCB_{11}Br_6H_6$) were of the highest quality available from Strem Chemicals (Newburyport, Mass.). Chloride salts of sodium and calcium, and nitrate salts of cadmium and copper, were puriss quality from Fluka. Lead nitrate, sodium hydroxide, and sodium bisulfite were ACS grade from Fisher Scientific (Norcross, Ga.). All salt solutions were made with deionized Nanopure water (18 MΩ·cm specific resistance).

Trifluoromethanesulfonic acid (99%), bromine (99.8%), and iodine monochloride were purchased from Alfa Aesar (Ward Hill, Mass.). Iodine was obtained in the highest purity available from Mallinckrodt-Baker (Phillipsburg, N.J.). Trimethylammonium chloride (98%), octadecanoic acid chloride, 4-aminoazobenzene, triethylamine (99.5%), and lithium aluminum hydride were acquired from Aldrich. All solvents were ACS grade from Aldrich and used as received.

Synthesis: A thick-walled Pyrex tube was charged with $Cs[CB_{11}H_{12}]$ (0.08 g, 0.29 mmol), trifluoromethanesulfonic acid (1.0 mL, 11.3 mmol), and iodine monochloride (1.0 mL, 19.6 mmol). The tube contents were frozen with liquid nitrogen, sealed under vacuum, and placed in a furnace. The temperature was ramped at 0.5° C./min to 200° C. and maintained for 48 h. After cooling, the resultant brown residue was treated with a 5% NaOH solution until the pH of the solution reached approximately 7, causing the aqueous layer to clear. This was followed by extraction with diethyl ether (3×20 mL). The dark brown ether portions were combined, concentrated to 30 mL, and subsequently treated with 10% $NaHSO_3$ until the solution turned colorless. A concentrated solution of $Me_3NHCl$ was then slowly added to precipitate the trimethylammonium (TMA) salt of UCC. The precipitate was filtered, washed twice each with water (25 mL) and a mixture of $CH_2Cl_2$/hexanes (1:5, 25 mL), and then dried under vacuum to give [Me$_3$NH][1-H-CB$_{11}$Cl$_{11}$] as a white solid (yield 150 mg, 89%). TMAUCC was characterized using ESI-MS, and FTIR. Elemental analysis calculated for $C_4H_{11}NB_{11}Cl_{11}$ (582.82): Theoretical: C, 8.24; H, 2.04; N, 2.40; Found: C, 8.50; H, 2.05; N, 2.32.

EXAMPLE 9

Synthesis of [Me$_3$NH][1-H—CB$_{11}$Br$_{11}$]

A Pyrex tube was charged with Cs[CB$_{11}$H$_{12}$] (0.11 g, 0.40 mmol), trifluoromethanesulfonic acid (1.0 mL, 11.3 mmol), and bromine (1.0 mL, 19.4 mmol). The temperature was ramped at 0.5° C./min to 200° C. and maintained for 96 hours. TMAUBC was obtained as a white solid (yield 350 mg, 81%). ESI-MS, $^1$H-NMR (250 MHz, acetone-d$_6$), and FTIR were used to confirm product composition. Elemental analysis calculated for C$_4$H$_{11}$NB$_{11}$Br$_{11}$ (1071.00): Theoretical: C, 4.48; H, 1.11; N, 1.31; Found: C, 4.92; H, 1.15; N, 1.33.

EXAMPLE 10

Synthesis of [Me$_3$NH][1-H—CB$_{11}$I$_{11}$](UIC)

A Pyrex tube was charged Cs[CB$_{11}$H$_{12}$] (0.10 g, 0.69 mmol), trifluoromethanesulfonic acid (1.0 mL, 11.3 mmol), and I$_2$ (2.0 g, 7.9 mmol). The temperature was ramped at 0.5° C./min to 240° C. and maintained for 120 h. TMAUIC was obtained as a white-yellow solid (yield 980 mg, 90%). ESI-MS, and FTIR were used to confirm product composition. Elemental analysis calculated for C$_4$H$_{11}$NB$_{11}$I$_{11}$ (1588.74): Theoretical: C, 3.02; H, 0.75; N, 0.88; Found: C, 4.14; H, 0.82; N, 0.88.

EXAMPLE 11

Synthesis of [Me$_3$NH][1-H—CB$_{11}$H$_5$Br$_6$](HBC)

Approximately 100 mg of Ag[1-H—CB$_{11}$H$_5$Br$_6$] was dissolved in 2 mL of ethyl acetate. About 5 mL of an aqueous solution of saturated trimethylammonium chloride was added to the ethyl acetate solution resulting in the precipitation of AgCl in the aqueous phase. Evaporation of ethyl acetate resulted in the recovery of TMAHBC. Elemental analysis calculated for C$_4$H$_{16}$NB$_{11}$Br$_6$ (676.58): Theoretical: C, 7.10; H, 2.39; N, 2.07; Found: C, 9.93; H, 2.62; N, 2.04.

The procedure for the synthesis of ETH 5315 has previously been described (90), and gave a yield of 163 mg (20%). The structure was confirmed by $^1$H-NMR (250 MHz, CDCl$_3$) and FAB-MS.

EXAMPLE 12

Optode Leaching Experiments

Cocktails (240 mg total weight) containing 33 wt. % PVC, 66 wt. % DOS, and 10 mmol/kg each of ETH 5315 (1.1 mg), and ion-exchanger, specifically, 2.2 mg NaTFPB, 3.8 mg (UIC), 2.6 mg (UBC), 1.4 mg (UCC), or 1.6 mg (HBC) were dissolved in 1.8 mL of THF. Using 200 μL aliquots from each cocktail, two membranes of the same composition were cast onto two 35 mm quartz disks by means of a spin-coating device (16). After air-drying the films for one hour they were placed in a flow-through cell, which was mounted into a Hewlett-Packard 8452A diode array UV-VIS spectrophotometer and filled with 0.2 M HOAc. The solution was continuously replaced at a rate of 1.2 mL/min. Absorption spectra were recorded between 300 and 800 nm at one minute intervals, with the exception of the films containing HBC, for which the absorbance was recorded every 15 seconds because of the rapid leaching behavior observed. Replicate experiments were performed to confirm the leaching behavior of each ion-exchanger.

EXAMPLE 13

Electrode Preparation and EMF Measurements of Polymers Comprising Halogenated Dodecacarborane Cation Exchangers For segmented sandwich membrane studies, cocktails (140 mg total weight) contained 10 mmol/kg ion-exchanger, i.e., TMA salts of carboranes or NaTFPB (0.9–1.1 wt %), plasticizer DOS or o-NPOE 66 wt % and PVC 33 wt %. ISE membranes of ca. 200 μm thickness were prepared by pouring the cocktails, dissolved in 1 mL of THF, into 22 mm glass rings affixed onto glass plates. After solvent evaporation, membranes containing carboranes were preconditioned in $10^{-2}$ M LiOH overnight in order to deprotonate the trimethylammonium cation and extract trimethylamine into the aqueous phase. Afterwards, the membranes were conditioned overnight in either 10–1 M KCl or CaCl$_2$ solutions. Disks 6 mm in diameter were cut from the parent membrane and assembled into Philips Electrode bodies. The internal filling solutions used were $10^{-1}$ M KCl or CaCl$_2$ depending on the composition of the conditioning solution. The measuring protocol followed has previously been reported (57, 58). Single membrane potentials were determined for each membrane containing either TFPB or a carborane anion. Then, the membranes were fused together with the TFPB-containing membrane in contact with the inner solution and the carborane-containing membrane in contact with the sample. The cell assembly used in this work was: IFS (0.1M M$^{z+}$Cl$_{z+}$)|TFPB|Carborane|sample (0.1M M$^{z+}$Cl$_{z+}$) where M$^{z+}$ is either K$^+$ or Ca$^{2+}$. Measurements were done in triplicate for each carborane evaluated and the means and standard deviations are reported.

For determination of the pK$_a$ of ETH 5315, the segmented sandwich membrane method was employed as previously described (61). Membranes were prepared as mentioned above and contained PVC-DOS (1:2) and either 10 mmol/kg chromoionophore and 5 mmol/kg NaTFPB or 5 mmol/kg TFPB only. In contrast to the previous report, a symmetric cell was used, with both the IFS and the sample consisting of 0.01 M HCl. Measurements for pK$_a$ determinations were done in triplicate and the mean and standard deviation are given.

For neutral carrier-based ISEs containing Pb$^{2+}$ Ionophore IV and an ion-exchanger, cocktails (140 mg total weight) consisted of 10 mmol/kg ionophore, 5 mmol/kg ion-exchanger, 33 wt. % PVC and 66 wt. % DOS, and were dissolved in 1.5 mL of THF. Membranes were fashioned according to the protocol mentioned previously and were conditioned overnight in $10^{-2}$ M NaCl. The electrodes were conditioned in NaCl solutions so that unbiased selectivity coefficients could be determined. Disks 4 mm in diameter were cut from the parent membrane and glued to PVC tubing using a PVC/THF slurry according to the technique reported by Ceresa et. al. (62). The inner filling solution used was $10^{-2}$ M NaCl. Five electrodes were evaluated for each ion-exchanger measured and the mean values and standard deviations are given for response slopes and selectivity coefficients. Selectivity coefficients were determined using the separate solution method (SSM). Before exposure to Pb$^{2+}$, electrode responses were measured towards Ca$^{2+}$, Na$^+$, Cd$^{2+}$, and Cu$^{2+}$ (from the most to least discriminated ion), according to previous recommendations (3, 63–65). Calibration curves were obtained from $10^{-4}$ M to $10^{-1}$ M and the potential of each ion at 1 M activity was extrapolated from the linear regression of the Nernstian response region.

All EMF measurements were made against a Ag/AgCl reference electrode (Metrohm 6.0729.100) with a 1M LiOAc bridge electrolyte. The instrumentation used to acquire potentiometric data has been described earlier (65). Measurement values were corrected for liquid junction potentials using the Henderson formalism and ion activities were calculated according to the Debye-Huckel approximation (66).

EXAMPLE 14

Computational Details

The $1\text{-HCB}_{11}X_{11}^-$ (X=Cl, Br, I) and $1\text{-HCB}_{11}H_5Br_6^-$ were optimized at the AM1 level of theory[39] within the Gaussian program (67). The electrostatic potentials were plotted onto the 0.001-au electron density contour at the STO-3G level using the Spartan® program (68). The plots are color-coded with each color indicating the interaction energy (kcal/mol) for a unit positive charge (see legend). The natural population analysis (NPA) charges (69–71) were computed at the B3LYP/3–21G(d)/AM1 level (wave function computed at the B3LYP/3–21 G(d) level at AM1 geometries).

Results and Discussion

This invention demonstrates that the MMA-DMA copolymer is a suitable matrix for preparing plasticizer-free polymers with grafted ionophores. Covalent grafting of hydrophilic crown ether-type ionophores illustrated an improvement in sensor sensitivity and selectivity relative to membranes containing entrapped ionophores. It has also been shown herein for the first time that 3-oxapentanediamide-type calcium ionophores can effectively be immobilized in MMA-DMA, while maintaining Nernstian response slopes for calcium and a relatively high selectivity. The polymer is plasticizer-free, and represents, with the exception of the lipophilic ion-exchanger, an all-polymeric calcium ion-sensing matrix.

The functionality of MMA-DMA as a polymer matrix for ISE membranes containing a covalently immobilized ionophore was initially tested with the model ionophores AAB15C5 and AAB18C6. These crown ether ionophores are commercially available and hydrophilic in nature, and an apparent improvement in function and selectivity should be observed if the resultant copolymer retains it function and physical properties. These $K^+$-selective ionophores were also selected because they have a very simple 1:1 binding stoichiometry and because their covalent attachment into an MMA-nBA matrix has already been reported (38). Moreover, it was of interest to determine whether or not a selectivity improvement would result using MMA-DMA, which was the case when sodium ion-selective ISEs were compared with another plasticizer-free matrix (25).

Tables 1 and 2 show the response and selectivity improvement of the grafted ionophores relative to the MMA-DMA membranes containing free ionophore. The dynamic range of ISEs containing grafted AAB18C5 and AAB18C6 was from $10^{-5}$–$10^{-1}$ M $K^+$. The favorable improvement in sensor function must be due to the retention of the ionophore through covalent anchoring. It is also noteworthy to mention that the selectivity observed was directly comparable to that previously reported for an MMA-nBA matrix, and it was superior to that reported for the unbound ionophore in PVC-NPOE membranes (35).

TABLE 1

Response slopes and potentiometric selectivity coefficients of MMA-DMA membranes comprising free and covalently grafted 4'-acryloylamidobenzo-15-crown-5, compared to literature data.

| Ion | Free in MMA-DMA slope | Free in MMA-DMA log $K^{pot}_{K,J}$ | Bound in MMA-DMA slope | Bound in MMA-DMA log $K^{pot}_{K,J}$ | Free in PVC-NPOE[a] log $K^{pot}_{K,J}$ | Bound in MMA-nBA[a] log $K^{pot}_{K,J}$ |
|---|---|---|---|---|---|---|
| $Mg^{2+}$ | 21.9 ± 1.0 | −2.2 ± 0.2 | 24.7 ± 2.0 | −4.1 ± 0.1 | −2.8 | −4.2 |
| $Ca^{2+}$ | 26.4 ± 3.0 | −2.0 ± 0.3 | 24.4 ± 1.6 | −4.2 ± 0.1 | −2.5 | −4.3 |
| $Na^+$ | 50.9 ± 1.4 | −0.8 ± 0.2 | 47.4 ± 1.5 | −2.0 ± 0.1 | −0.5 | −2.0 |
| $K^+$ | 51.4 ± 0.8 | 0 | 56.1 ± 1.3 | 0 | 0 | 0 |

[a]See Ref (35)

TABLE 2

Response slopes and potentiometric selectivity coefficients of MMA-DMA membranes comprising free and covalently grafted 4'-acryloylamidobenzo-18-crown-6, compared to literature data.

| Ion | Free in MMA-DMA slope | Free in MMA-DMA log $K^{pot}_{K,J}$ | Bound in MMA-DMA slope | Bound in MMA-DMA log $K^{pot}_{K,J}$ | Free in PVC-NPOE[a] log $K^{pot}_{K,J}$ | Bound in MMA-nBA[a] log $K^{pot}_{K,J}$ |
|---|---|---|---|---|---|---|
| $Mg^{2+}$ | 19.5 ± 2.5 | −2.4 ± 0.3 | 18.0 ± 1.7 | −4.4 ± 0.1 | −3.5 | −4.5 |
| $Ca^{2+}$ | 19.1 ± 1.6 | −2.1 ± 0.1 | 21.0 ± 1.8 | −4.1 ± 0.1 | −3.1 | −4.3 |
| $Na^+$ | 34.5 ± 2.8 | −1.2 ± 0.1 | 47.2 ± 2.1 | −1.8 ± 0.1 | −1.5 | −1.7 |
| $K^+$ | 50.7 ± 3.1 | 0 | 56.9 ± 1.5 | 0 | 0 | 0 |

[a]See Ref (35)

In order to make an MMA-DMA polymer containing a grafted calcium ionophore, a novel ionophore of this invention, AU-1, with a polymerizable acrylic group was synthesized. AU-1 is a derivative of ETH 129, which is a well-known calcium ionophore with an extremely high calcium selectivity (72, 3). The novel ionophore of this invention maintains the general structure of 3-oxapentanediamide, which forms a stable 3:1 complex with calcium (72).

Initial potentiometric characterization of the ionophore was accomplished using DOS and NPOE-plasticized PVC membranes containing 20 mmol/kg of free ionophore and 5 mmol/kg of NaTFPB. The electrodes showed Nernstian responses towards calcium with slopes of 29.4 mV/decade and 31.2 mV/decade, respectively. Linear response ranges from $10^{-5}$–$10^{-1}$ M $Ca^{2+}$ were observed. No attempt was made to optimize the electrodes for low detection limit applications.

The selectivity of the AU-1 in PVC-DOS and PVC-NPOE membranes was measured using the protocol for the determination of unbiased selectivity coefficients (see Table 3) (3). The ionophore showed excellent calcium selectivity, although it was somewhat worse than that reported for free ETH 129 (3).

A plasticizer-free membrane made from MMA-DMA, containing 20 mmol/kg of free AU-1 and 5 mmol/kg of NaTFPB was also measured. The polymer membrane showed a Nernstian response for $Ca^{2+}$ from $10^{-5}$–$10^{-1}$ with a slope of 29.5 mV/decade. As shown in Table 3, the unbiased selectivity of the plasticizer-free ISE was found to be reduced compared to that observed for plasticized PVC membranes. This is consistent with the results for ETH 129 under the same conditions, as recently reported (25). However, the slopes for the interfering ions in the MMA-DMA membrane are sub-Nernstian, which is known to bias the calculated selectivity (3). It is often the case that plasticizer-free polymer matrices have higher membrane resistances than plasticized PVC membranes (21). This may originate from a decreased diffusion coefficient of ions within the membrane, which may hamper the required complete interfacial exchange with highly discriminated ions in selectivity determinations. On the other hand, the observed decreased selectivity may also originate from changes in the complex formation constants in the altered polymer matrix.

affinity of this ionophore can be obtained. The membrane potential $E_M$ is determined by subtracting the cell potential for a membrane without ionophore from that for the sandwich membrane. The formation constant of the ionophore with the primary ion is then calculated from the following Equation (1):

$$\beta_{ILn} = (L_T - nR_T/z_I)^{-n} \exp(E^M z_I/RT) \tag{1}$$

where $L_T$ is the total concentration of ionophore in the membrane segment, $R_T$ is the concentration of lipophilic ionic site additives, n is the ion-ionophore complex stoichiometry, and R, T, and F are the gas constant, the absolute temperature, and the Faraday constant, respectively (57). The primary ion I carries a charge of $z_I$. The ionophore ETH 129 and its derivatives have been shown to form strong complexes with calcium with a binding stoichiometry of 3:1 (72). For this reason, the complex formation constants of unbound AU-1 with the primary ion, $Ca^{2+}$, in PVC-DOS, PVC-NPOE and MMA-DMA membranes were measured using the sandwich membrane method. The stability constants for AU-1 and ETH 129 in different polymer matrices are compared, under otherwise the same experimental conditions, in Table 4.

TABLE 4

Sandwich membrane potentials and complex stability constants free of AU-1 and ETH 129 with calcium ions in various polymer matrices.

| | Free AU-1 | | Free ETH 129 | |
|---|---|---|---|---|
| Membrane | ΔEMF [mV] | $\log\beta_3$ | ΔEMF [mV] | $\log\beta_3$ |
| PVC-DOS | 437 ± 1 | 20.49 ± 0.04 | 586 ± 4 | 25.50 ± 0.12 |
| PVC-NPOE | 519 ± 2 | 23.26 ± 0.09 | 692 ± 4 | 29.20 ± 0.12 |
| MMA-DMA | 359 ± 9 | 17.9 ± 0.3 | | |

The stability constants of the ionophores in DOS membranes are lower than in NPOE membranes. DOS possesses two ester groups that are in principle capable of binding to cationic species. Furthermore, it solvates the extracted cations in ionophore-free membranes and membrane segments

TABLE 3

Response slopes and potentiometric selectivity coefficients of MMA-DMA membranes comprising free and covalently immobilized AU-1 in different polymer matrices.

| | Free in PVC-DOS | | Free in PVC-NPOE | | Free in MMA-DMA | | Bound in MMA-DMA | |
|---|---|---|---|---|---|---|---|---|
| Ion | slope | $\log K^{pot}_{Ca,J}$ | slope | $\log K^{pot}_{Ca,J}$ | slope | $\log K^{pot}_{Ca,J}$ | slope | $\log K^{pot}_{Ca,J}$ |
| $K^+$ | 59.3 ± 1.8 | −6.2 ± 0.2 | 56.2 ± 2.1 | −7.8 ± 0.1 | 49.7 ± 1.4 | −4.2 ± 0.2 | 38.5 ± 1.1 | −4.3 ± 0.1 |
| $Na^+$ | 57.0 ± 2.0 | −4.9 ± 0.2 | 52.1 ± 2.6 | −6.0 ± 0.2 | 45.3 ± 1.5 | −3.5 ± 0.1 | 36.8 ± 2.5 | −3.3 ± 0.2 |
| $Mg^{2+}$ | 27.1 ± 1.2 | −8.8 ± 0.2 | 31.4 ± 1.5 | −8.7 ± 0.2 | 25.2 ± 2.2 | −5.8 ± 0.2 | 20.3 ± 2.3 | −4.6 ± 0.1 |
| $Ca^{2+}$ | 29.4 ± 1.9 | 0 | 31.2 ± 2.1 | 0 | 0.31.6 ± 1.8 | 0 | 32.1 ± 1.0 | 0 |

The sandwich membrane technique has been demonstrated to be a good method for studying the binding properties of ionophores within ISE membranes (57, 58, 73). As established in previous work, transient membrane potential measurements on fused segmented sandwich membranes yield information about the activity ratio on both sides of the membrane. If only one side contains a known concentration of ionophore, information about the binding more strongly than NPOE-based membranes, which results in the occurrence of smaller binding constants (74).

The MMA-DMA copolymer has a low dielectric constant (E=3) (75) and numerous pendant ester groups similar to DOS (E=4) (2), which makes MMA-DMA membranes behave more like PVC-DOS than PVC-NPOE (19). Interestingly, the stability constants of the ionophore in MMA-DMA are even lower than in DOS. The lower stability constant for the novel calcium ionophore AU-1 of this invention is, in fact, a favorable characteristic. For example, it is known that calcium-selective membranes containing traditional calcium ionophores such as ETH 129 may suffer from severe anion interference at high concentrations (76). Moreover, optical calcium sensors containing ETH 129 are not operational at physiological pH because of the high stability constant for this ionophore, and the fact that H$^+$-chromoionophores with higher basicities have not been explored for this application. A higher basicity would shift the measuring range to more desirable concentrations, since these optodes function on the basis of a competitive exchange equilibrium between calcium and hydrogen ions.

The sufficient selectivity of AU-1 and the fact that AU-1 contains a polymerizable acrylic group makes this novel compound very suitable for preparing a plasticizer free polymer with a grafted AU-1 ionophore. Various polymers with different amounts of grafted AU-1 (1 wt %, 2 wt %, and 5 wt %) were evaluated.

The membranes containing 1 wt % immobilized AU-1 showed a Nernstian calcium response slope, but exhibited poorest calcium selectivity, with the experimental selectivity coefficients log $K_{Ca, Mg}^{pot}$=−2.8±0.1, log $K_{Ca, Na}^{pot}$=−1.2±0.1 and log $K_{Ca, K}^{pot}$=−0.9±0.1 (n=3). The membranes with 2 wt % AU-1 showed much better selectivity, with log $K_{Ca, Mg}^{pot}$=−4.7±0.1, log $K_{Ca, Na}^{pot}$=−3.1±0.1 and log $K_{Ca, K}^{pot}$=−3.3±0.1 (n=3). However, the polymer prepared with 5 wt % (98 mmol/kg) AU-1 showed the best mechanical properties and superior response characteristics for calcium compared to the other two polymer batches (see below), and was therefore this polymer formulation was used in subsequent experiments. The presence of the AU-1 in the polymer was confirmed by H$^1$NMR (data not shown). The amount of immobilized ionophore was estimated by measuring the relative NMR intensities of the protons that corresponded to the ionophore (35). The estimated ionophore concentration for the polymer containing 5 wt % AU-1 was determined as 90 mmol/kg, indicating that 92% of the ionophore had been polymerized.

The ISE containing 5 wt % AU-1 showed a Nernstian response for Ca$^{2+}$ from 10$^{-5}$–10$^{-1}$ M with a slope of 32.1 mV/decade (see Table 3). Response times were on the order of 2 min, and therefore reasonably rapid. The immobilization of the ionophore did not change the slope of the calibration curves for the primary ion, and the selectivity of calcium over sodium and potassium ions was comparable to MMA-DMA membranes containing free ionophore.

The decreased discrimination of magnesium ions by AU-1 is an interesting characteristic that deserves discussion. The unmodified 3-oxapentanediamide ETH 129 ionophore is known to form 3:1 complexes with calcium, and the same is expected for its derivative AU-1. The graft polymer MMA-DMA-AU-1 was prepared by copolymerization of the three different monomers, probably leading to a random distribution of immobilized AU-1 within the linear polymer chains. The free energy to bring the immobilized AU-1 ionophore units into optimal binding conformation for calcium is expected to be higher in comparison to polymers with unbound AU-1. This should lead to a weakening of the calcium binding strength and to a somewhat decreased selectivity. The requirement of polymer rearrangement for optimal calcium selectivity may also explain the lower selectivity for the membranes containing lower ionophoric monomer loading. Nonetheless, the selectivity for the 5 wt % polymer batch appears to be adequate for accurate calcium determinations in a variety of samples.

It was attempted to estimate the calcium complex formation constant of immobilized AU-1 in the membrane phase. As with the unbound AU-1 experiment described above (Table 4), the binding study was performed with the sandwich membrane technique. This binding study was semi-quantitative because the exact structure and concentration of AU-1 in the final membrane was not accurately known. Upon fusion of the AU-1 containing copolymer with AU-1-free MMA-DMA, a 310.8±0.8 mV potential increase was observed, which was somewhat smaller than for unbound AU-1 (see above). This leads to a lower estimated complex formation constant of log β3=16.85±0.03.

Figure 2:
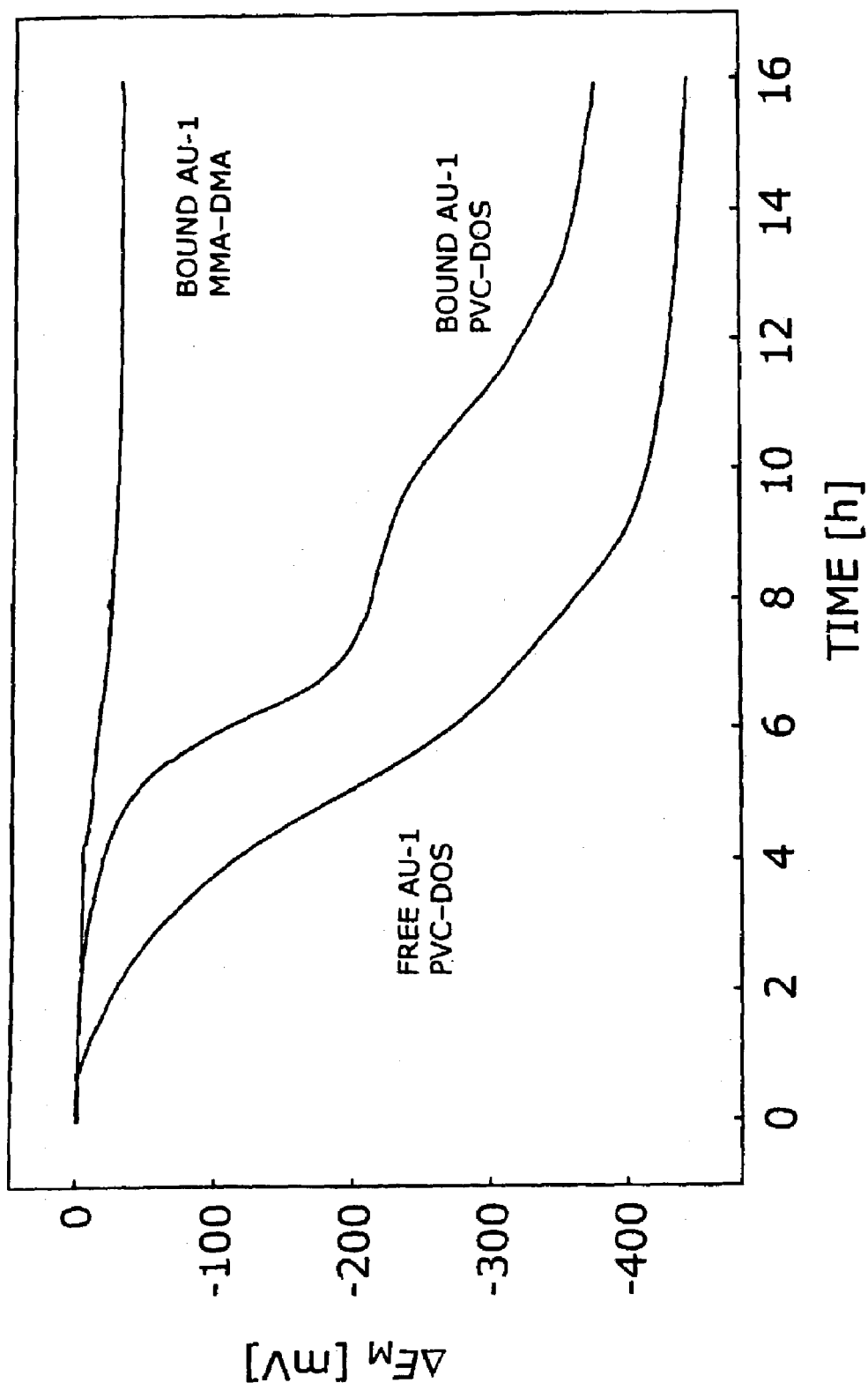
FIG. 2 is a graph showing the time-dependent membrane potential versus time for a MMA-DMA-AU-1 graft polymer, a membrane comprising AU-1 blended with PVC-DOS, and a PVC-DOS membrane containing free AU-1.

FIG. 2 shows the sandwich membrane potential-time response after initial contact of the two segments, which is known to reflect the diffusion kinetics of the ionophore toward the undoped segment side. With freely dissolved ionophore in plasticized PVC membranes, the initial potential (shown in FIG. 2 as 0 mV) is stable for about 20 minutes before the potential starts to decrease, owing to ionophore reaching the other membrane side and starting to change that phase boundary potential. Here, however, the potential was essentially stable for more than 16 hours, confirming that the copolymer diffused at a drastically slower rate than freely dissolved ionophore. The small potential drift observed between 5 and 8 h of the experiment cannot reliably be assigned to an ionophore diffusion process because the potential was found to be stable again at longer times.

In a second experiment, 10% of the MMA-DMA-AU-1 copolymer was blended with 90% PVC-DOS. The reference segment contained only PVC-DOS and the same concentration of cation-exchanger. FIG. 2 is a graph showing the time-dependent membrane potential versus time for a MMA-DMA-AU-1 graft polymer, a membrane comprising AU-1 bound to PVC-DOS, and a PVC-DOS membrane containing free AU-1. Longer potential stabilities at zero volts are indicative of a lower mobility of the ionophore.

The 413±1 mV change found upon fusion of the two segments corresponds to a logarithmic stability constant of 20.31±0.04, which is essentially the same as for unmodified AU-1 in PVC-DOS (see above). The potential was stable for about 4 hours (see FIG. 2), indicating that the copolymer diffuses at a significantly slower rate than freely dissolved ionophore, but that the mobility is much higher than in plasticizer-free MMA-DMA membranes. A reference experiment was performed with unbound AU-1 in PVC-DOS, and also shown in FIG. 2. Indeed, the diffusion behavior was drastically faster for this case and was in agreement with valinomycin diffusion in the same matrix (57). Interestingly, the experiment with immobilized AU-1 shows two different apparent diffusion time constants, one slower and one faster, which is evidenced by the unusual potential-time profile between 6 and 15 hours. This could be an indication for a broad molecular size distribution of MMA-DMA-AU-1, with polymer chains that diffuse at different rates.

Another important sensing platform used in ion analyses is the bulk optode, which contains a selective, lipophilic ionophore, a chromoionophore and ionic sites entrapped within a polymeric film that is coated onto a glass support. The good film-forming properties of MMA-DMA polymers make them suitable materials for preparing plasticizer free optodes, as recently reported by Peper et al. (77). The optode thin films made from MMA-DMA-AU-1 also contained a H$^+$-selective fluoroionophore (ETH 5294) and NaTFPB. Optical characterization of the films was done via fluorescence microscopy/spectroscopy. The sensing principle employed to assess optode function is based on an ion-exchange mechanism shown in Equation (2):

$$Ind(org) + 2L_3Ca^{2+}(org) + H^+(aq) + R'(org) = IndH^+(org) + 3L(org) + 2Ca^{2+}(aq) + R^-(org) \quad (2)$$

where Ind is a neutral chromoionophore, L is an ionophore, R are anionic sites, respectively (59). The organic film phase and the aqueous phase are indicated as (org) and (aq), respectively. When the optode film comes in contact with calcium ions they are extracted into the film and concomitantly exchanged with hydrogen ions in order to conserve electroneutrality within the film. The change in the degree of protonation of the fluoroionophore, which is a result of proton release from the film, leads to a measurable change in its fluorescence properties. Emission peaks were observed at 647 nm and 683 nm. The former corresponds to the protonated form of ETH 5294, while the latter corresponds to the deprotonated form. When the concentration of $Ca^{2+}$ in the sample increases the protonated peak at 647 nm decreases and the deprotonated peak at 683 nm increases (see Eq. 2). It has been reported that ratiometric analysis can minimize the effects of photobleaching and variations in lamp intensity (12), therefore, the intensity ratio of the two peaks (647 and 683 nm) was used instead of absolute fluorescence.

The response of the films based on an ion-exchange equilibrium, given as a function of the experimentally accessible mole fraction of unprotonated chromoionophore $\alpha$, is written as shown in Equation (3):

$$\alpha_I = (z_1 K_{exch})^{-1} (\alpha a_H / 1 - \alpha)_I^{z_I} \frac{[R_T^- - (1-\alpha)C_T]}{\{L - (R_T^- - (1-\alpha)C_T)(n/z_1)\}^n} \quad (3)$$

where $I_T$, CT and $R^-_T$ are the total concentrations of ionophore, chromoionophore and lipophilic ion-exchanger, respectively, and $K_{exch}$ is the ion-exchange constant (59, 78). The latter is a function of the ion-ionophore complex formation constant, the $pK_a$ of the chromoionophore and the free energies of transfer of the exchanging cations.

Figure 3:
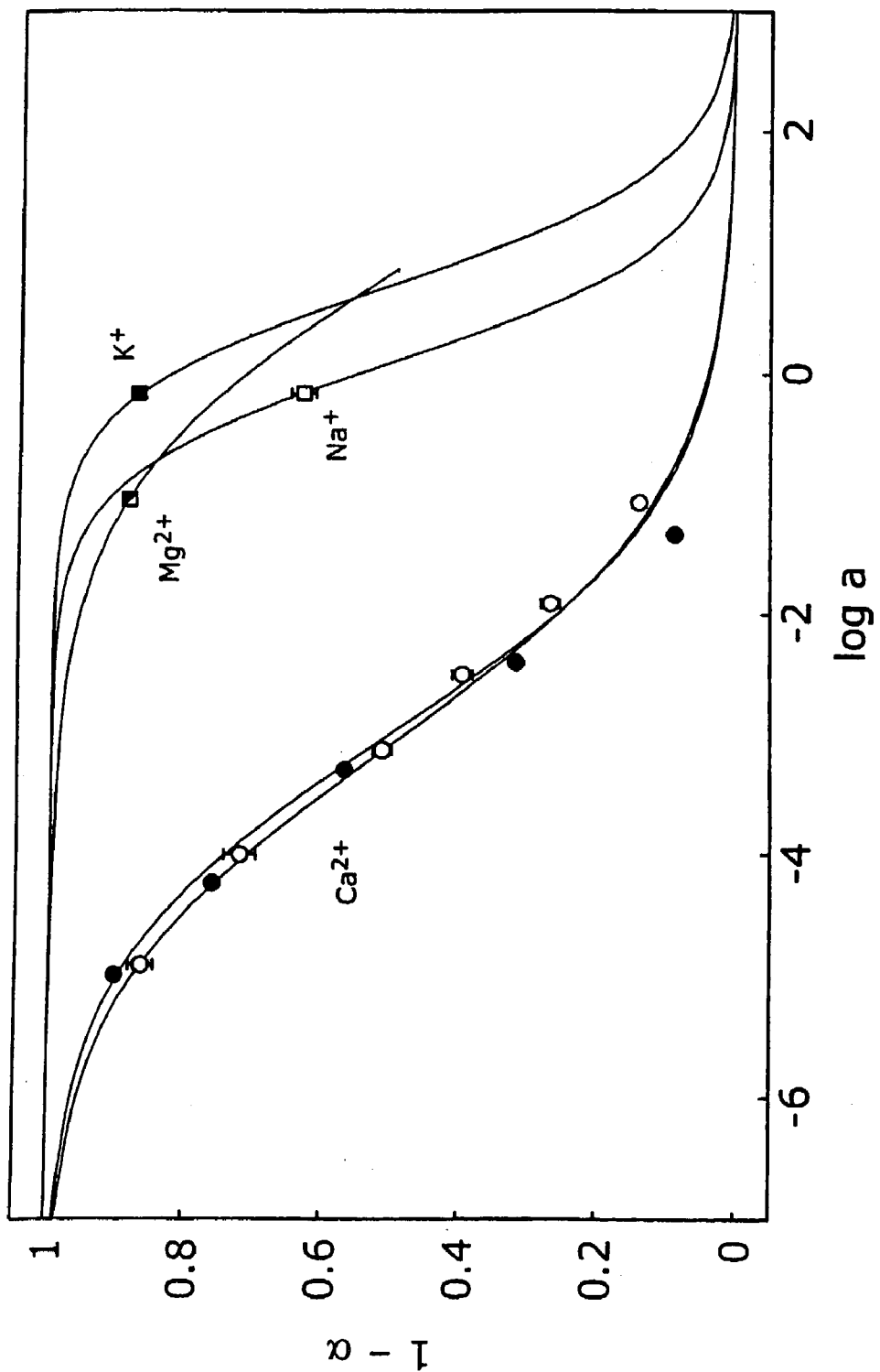
FIG. 3 is a graph of optode response curves and selectivity of an MMA-DMA-AU-1 optode film towards calcium ions (open circles). Filled circles represent the optical calcium responses for a 1:9 blend of MMA-DMA-AU-1 and PVC-DOS.

FIG. 3 shows optical response curves and selectivities of a MMA-DMA-AU-1 copolymer containing NaTFPB and the chromoionophore ETH 5294 towards calcium (open circles), magnesium, potassium, and sodium ions measured at pH 6.5. The lines are theoretically predicted responses according to equation 3, with log $K_{exch}$=-8.7 for calcium ions (n=3), -8.0 for potassium ions (n=1), -7.35 for sodium ions (n=1), and -13.8 for magnesium ions (n=2). Filled circles represent the optical calcium responses for a 1:9 blend of MMA-DMA-AU-1 and PVC-DOS, with a theoretical curve according to Eq. 3 with log $K_{exch}$=-5.4.

The response curve generated with MMA-DMA-AU-1 corresponds well to the theoretically predicted response. The observed ion-exchange constant was found to be log $K_{exch}$=-8.7. This value, compared to literature data (37), again indicates that complexes with the immobilized ionophore are significantly weaker than with ETH 129. For this particular application, this is a favorable characteristic. The weaker calcium complexation shifts the calcium response range, for the first time, to physiological conditions. Indeed, at pH 7.0, theory predicts that the dynamic range for this optode is between $10^{-6}$ and $10^{-2}$ M calcium. Previous reports on calcium electrodes required a pH of 5.4 for physiological measurements. As expected from the diffusion experiments shown in FIG. 2, optode response times were longer than with unbound ionophores. Typical response times were on the order of 20 min and varied with the batch of polymer produced. This limitation is expected to be much less of an issue with ultraminiaturized systems, where the drastically smaller diffusion distances will give much faster response times than with the films studied here. Instead, solving leaching and cross-contamination problems will be most important goals in those cases.

As indicated in by the dotted lines in FIG. 3, magnesium, potassium and sodium ions were all well discriminated. The observed selectivity log $K^{Osel}_{Ca,J}$ of calcium over the interfering ions was measured in 1 M cation chloride salts solution at the same pH as for the calcium curve. The selectivity coefficient for calcium over magnesium, potassium and sodium ions was -3.8, -3.7, and -3.1 respectively (at half protonation of the chromoionophore). The respective $logK^{opt}_{IJ}$ values for these three interfering ions, which can be directly compared to ISE selectivity coefficients (79), are calculated as -3.8, -4.5 and -2.8. The selectivity compares very well to the corresponding ISE (see Table 3).

The sandwich membrane diffusion studies discussed above (see FIG. 2) had indicated that the AU-1 containing copolymer is compatible with small amounts of PVC-DOS, and that its diffusion coefficient is significantly larger than in the plasticizer free MMA-DAM-AU-1 polymer matrix alone. This suggests that optodes containing a blend of the copolymer and PVC-DOS should exhibit faster response times as well. Indeed, the blending of the two different polymer matrices was successful and yielded homogenous optode films by spin coating. Response times were visually found to be less than 2 min, which was on the same time scale as optode films containing freely dissolved components. The exchange constant for the optical calcium response curve was found as log $K_{exch}$=-5.4. The calcium response curve was close to the one for the MMA-DMA copolymer, and shown in FIG. 3 as filled circles. Since the ionophore was 10-fold diluted in the case of the blended polymer system, it is an additional indication that calcium complexes are weaker for the copolymer than for the PVC-DOS blend. This is in reasonable correspondence with the results from the sandwich experiments discussed above, where the polymer blend also showed complexes that were about 3 orders of magnitude stronger than with the pure copolymer system.

Using a molecular imprinting technique, highly crosslinked polymers with $Ca^{2+}$ and $Mg^{2+}$ as the templates were prepared with the functional monomer of this invention is the novel polymerizable derivative of ETH 129, i.e., AU-1. Since $Ca^{2+}$ and $Mg^{2+}$ binds with oxapentanediamide type ionophores such as ETH 129 with only one stoichiometry, the ionophores can be immobilized with specific stoichiometry and the cavities left in the rigid polymer network can rebind with $Ca^{2+}$ and $Mg^{2+}$ selectively after removal of the templates.

AU-1 was used to prepare plasticizer free polymer with immobilized ionophore for ISE's and optodes. The complex formation constants of AU-1 with $Ca^{2+}$ and $Mg^{2+}$ in PVC-DOS membrane membranes were reported to be 20.49±0.04 and 14.87±0.02, respectively (50). The complexation between the ionophore and magnesium ion is relatively weaker than the binding with calcium, however, it is still a rather strong interaction compared with other ionophores such as valinomycin ($log\beta_{KL}^+$=10.10) (51). The selectivity of AU-1 in PVC-DOS and PVC-NPOE membrane was determined by unbiased selectivity measurements. The selectivity was close to but slightly worse than that for the ETH 129 membranes, which agrees well with their structure difference.

The imprinted polymers were prepared by precipitation polymerization. This method can produce polymer particles with size about 1 μm so that the traditional steps of grinding and sieving of the polymer are avoided. Four different polymers A–D were prepared with the composition shown in Table 5. Polymer A is the blank polymer without the functional monomer; polymer B was synthesized from functional monomer (AU-1), crosslinker (EGDMA) and spacer monomer (MMA) but without any template. Polymer C is the calcium ion imprinted polymer and polymer D is the magnesium ion imprinted polymer.

TABLE 5

| Polymer | Functional monomer (mol %) | EGDMA (mol %) | MMA (mol %) |
|---|---|---|---|
| A | 0 | 60 | 40 |
| B | 5 | 60 | 35 |
| C ($Ca^{2+}$) | 5 | 60 | 35 |
| D ($Mg^{2+}$) | 5 | 60 | 35 |

The amount of crosslinker is very important for preparing selective imprinted polymer. The smaller the ratio of template to crosslinker the higher is the selectivity of the imprinting polymer (80–82). At low degrees of crosslinking the selectivity is poor because the polymer is not crosslinked enough to retain the shape of the cavities. When EGDMA is used as crosslinker, the selectivity of the polymer increases sharply at about 40% (vol %) crosslinker and becomes stable at 60% (81, 83).

After polymerization, the imprinted polymers were extracted with a mixture of methanol and water to remove the templates. The resulting polymers were characterized by elemental analysis as shown in Table 6. For polymers B and C, the ionophores were immobilized and formed binding sites in the polymer in high yield. However, for the $Mg^{2+}$ imprinted polymer, the amount of immobilized ionophore was less than the expected value. This is probably due to the fact that some magnesium complexes disassociate and as a result lower the yield of polymerization.

TABLE 6

Elemental analysis of Polymers A–D

| Element | A (Blank) Theory | A (Blank) Found | B (AU-1 only) Theory | B (AU-1 only) Found | C ($Ca^{2+}$) Theory | C ($Ca^{2+}$) Found | D ($Mg^{2+}$) Theory | D ($Mg^{2+}$) Found |
|---|---|---|---|---|---|---|---|---|
| C | 60.44 | 59.72 | 61.67 | 59.73 | 61.67 | 59.06 | 61.67 | 59.88 |
| H | 7.33 | 7.33 | 7.25 | 7.13 | 7.25 | 7.11 | 7.25 | 7.35 |
| N | 0 | 0 | 0.78 | 0.85 | 0.78 | 0.72 | 0.78 | 0.20 |

The imprinted polymers were then tested in ion-selective electrodes by mixing with PVC and loading on the PVC tubing. The blank polymer A and B did not show selectivity to any ions and the potential only increase about 20 mV in the whole measuring range (data not shown). For polymer B the ionophores are diluted and immobilized in the crosslinked polymer network, which makes it difficult to form stable 3:1 complex with $Ca^{2+}$.

Figure 4:
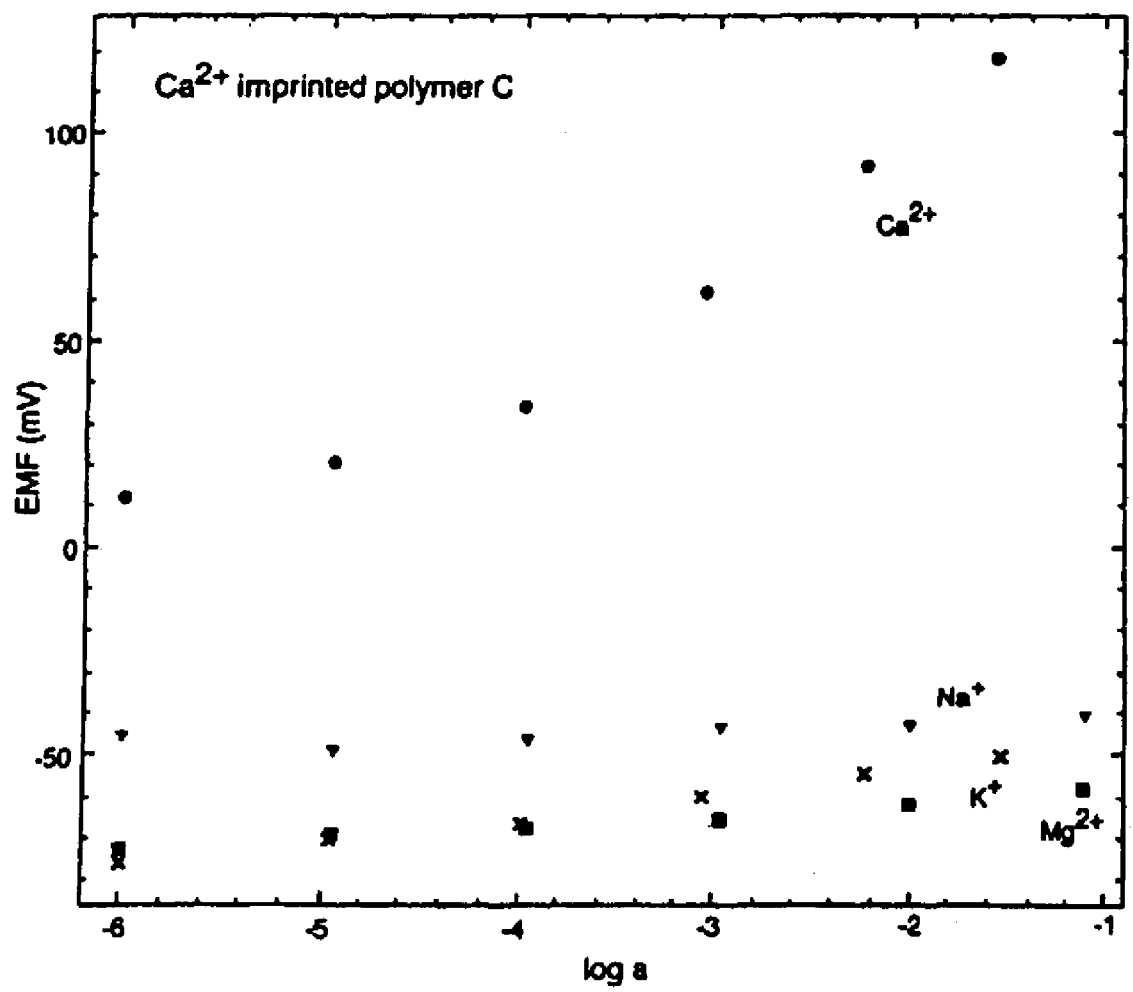
FIG. 4 is a graph of the potentiometric responses of a calcium ion-imprinted MMA-AU-1 copolymer imprinted with calcium ions.

FIG. 4 is a graph of the potentiometric responses of a calcium ion-imprinted MMA-AU-1 copolymer imprinted with calcium ions. FIG. 4 shows that the calcium ion imprinted polymer C exhibited good calcium selectivity. The measuring range is from $10^{-4.5}$ to $10^{-1}$ M and the selectivity is shown in Table 7.

TABLE 7

Responses and selectivities of the $Ca^{2+}$ imprinted polymer C and the $Mg^{2+}$ imprinted polymer D.

| | Polymer C | | Polymer D | |
|---|---|---|---|---|
| Slope (mV/decade) | 31.2 ± 1.0 | | 33.5 ± 2.1 | |
| Linear range | $10^{-4.5}$–$10^{-1}$ M | | $10^{-3.5}$–$10^{-1}$ M | |
| Log $K^{pot}_{I,J}$ | J $Mg^{2+}$ | −5.9 ± 0.2 | J $Ca^{2+}$ | −1.5 ± 0.1 |
| | (I:$Ca^{2+}$) $Na^+$ | −4.8 ± 0.1 | (I:$Mg^{2+}$) $Na^+$ | −1.1 ± 0.1 |
| | $K^+$ | −5.4 ± 0.1 | $K^+$ | −0.8 ± 0.1 |

The welled conditioned electrode give stable response in 2 minutes, which is slower than regular PVC membranes. The narrow working range and longer response time of the PVC membrane without plasticizer were reported before (84). The good calcium selectivity showed that the ionophores are pre-organized in a favorable position to bind calcium ions by imprinting of metal ions. Similarly, Rosatzin et al. reported that the binding strength was 6 times higher for $Ca^{2+}$ imprinted polymer than for the polymer without the template (44).

Figure 5:
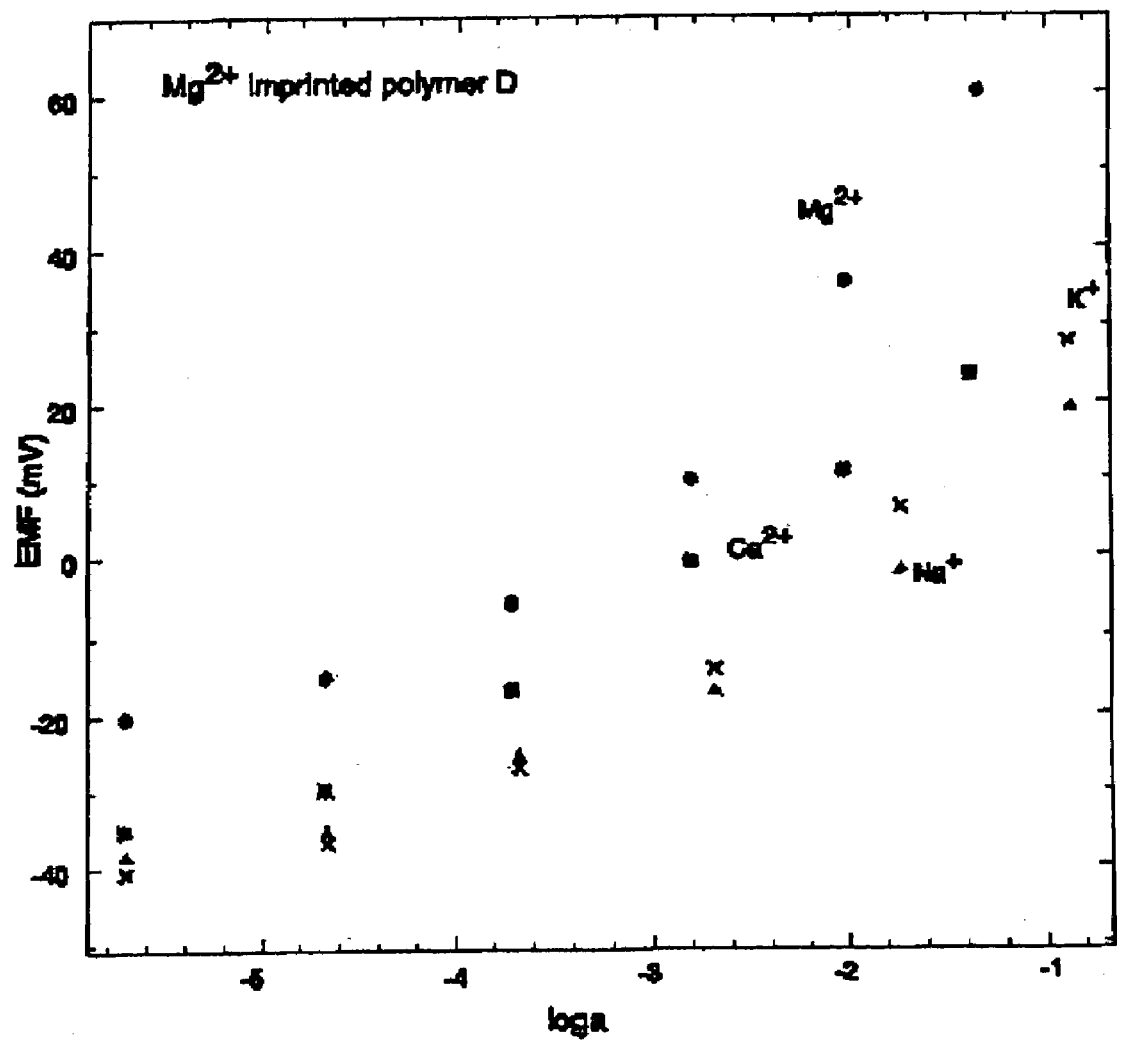
FIG. 5 is a graph of the potentiometric responses of a magnesium ion-imprinted MMA-AU-1 copolymer.
Figure 6A:
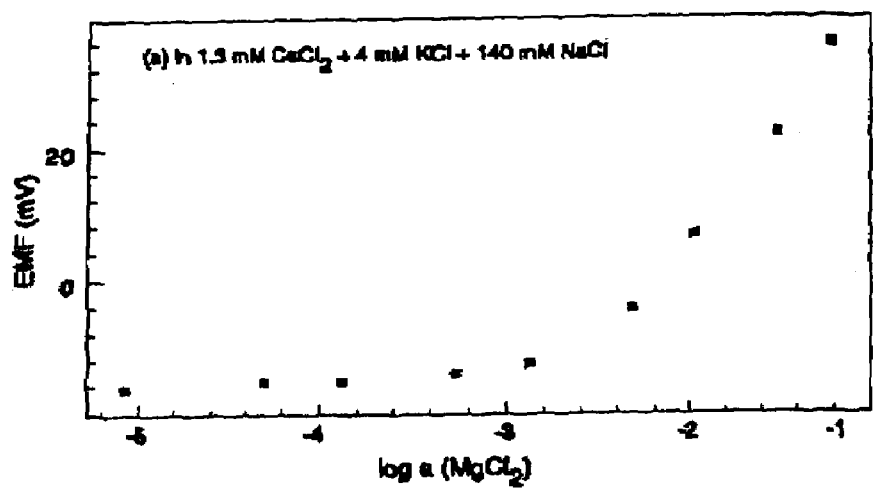
FIG. 6A is a graph of the potentiometric responses of a magnesium ion-imprinted MMA-AU-1 copolymer in a $CaCl_2$/KCl/NaCl solution.
Figure 6B:
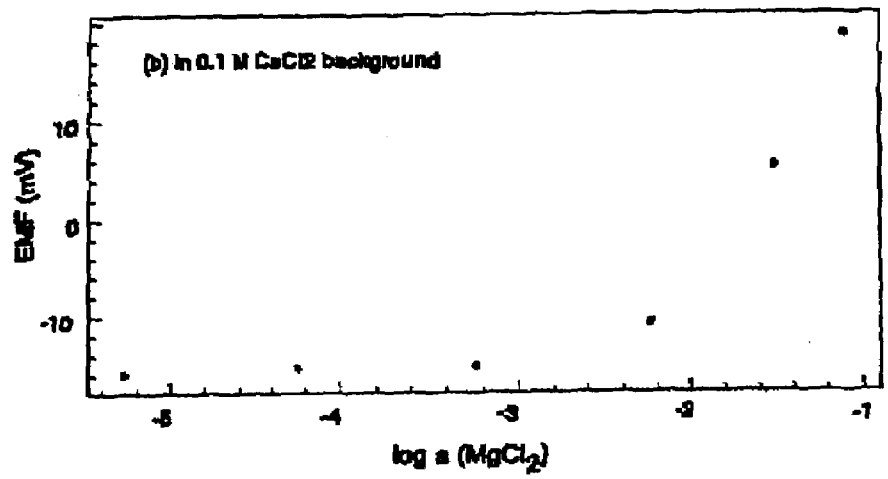
FIG. 6B is a graph of the potentiometric responses of a magnesium ion-imprinted MMA-AU-1 copolymer in a $CaCl_2$.

In contrast, magnesium ion imprinted polymer D showed magnesium selectivity with the measuring range from $10^{-3.5}$ to $10^{-1}$ M as shown in FIG. 5. Even in mixture solution or 1 M $CaCl_2$ background, the electrodes still showed magnesium selectivity as shown in FIGS. 6A and 6B. In FIG. 6B, the detection limit of the electrode in 0.1 M $CaCl_2$ as background was log $a_I(DL)=-2.5$, which gave the selectivity of $Mg^{2+}$ over $Ca^{2+}$ log $K^{sel}_{Mg,Ca}=-1.5$ (FIM). Obviously the dramatically changed selectivity is due to the imprinting effect. In contrast, Rosatzin et. al. did not observe the binding of magnesium ions under the conditions even for $Mg^{2+}$ imprinted polymer. This is probably due to the loss of binding sites in the grinding and sieving steps (42) or the limitation of equilibration experiments for measuring the binding strength of the polymers (44). In addition, the different functional monomer chosen may be another reason for the opposite results. The functional monomer used in Rosatzin's paper was N,N'-dimethyl-N,N'-bis(4-vinylphenyl)3-oxapentanediamide. The selectivity of this compound (SSM, (log $K^{pot}_{Ca,K}=-1.7$, (log $K^{pot}_{Ca,Na}=-1$–8; DOS) (44) indicated more interference from $Na^+$ and $K^+$ compared to the ETH 129 (SSM, (log $K^{pot}_{Ca,K}=-4.0$, (log $K^{pot}_{Ca,Na}=-3.6$; DOS) (4).

Thus, this invention demonstrates the first magnesium selective sensor prepared with a calcium ionophore, although the selectivity of $Mg^{2+}$ over other ions was not as good as other magnesium ionophores (18). Also the measuring ranges of the electrodes are narrow probably due to the nature of the rigid polymer matrix (84). It is well known that the ionic sites have important influence in the response and selectivity of the carrier based ISEs (1). However, it hadn't been used here because it is difficult to make solid mixture with ionic sites. The permselectivity of the imprinted polymers probably came from the anionic impurities in PVC or polymer.

Heterogeneous membranes with PVC, DOS, 20% (w/w) calcium ion imprinted polymer powder and different amount of NaTFPB were prepared and measured. However, none of them showed $Ca^{2+}$ selectivity, which is conflict with Murray's results for lead (II) sensor (46). It is possible that the imprinted polymer in PVC-DOS membrane is diluted and there is no sufficient contact and interaction with analytes. Increasing the amount of MIP polymer makes the membrane too brittle and loses the smooth surface so it is difficult to make electrode from it.

membrane technique was used to determine relative ion-pairing trends of the carborane anions within plasticized ISE membranes. In addition, computational methods were used to calculate electrostatic contours for the carboranes in the presence of an approaching point charge, and the charge density distribution for each ion-exchanger was determined using natural population analysis. Slope and selectivity of electrodes containing the ion-exchangers and tert-butylcalix[4]arene-tetrakis(N,N-dimethylthioacetamide) were used to evaluate response characteristics.

Figure 7:
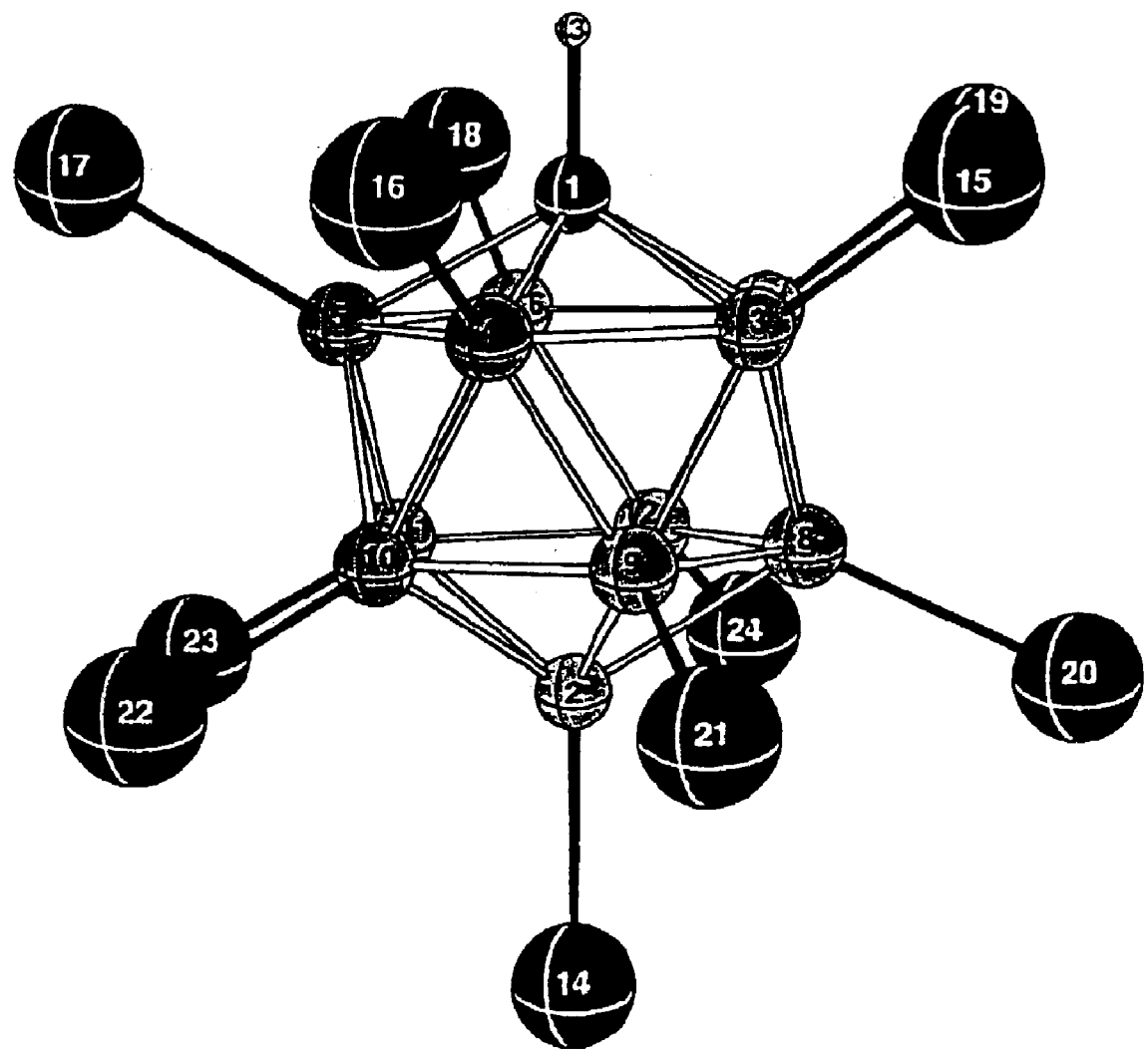
FIG. 7 shows a three-dimensional chemical structure of the carba-closo-dodecacarborane anions. Atoms 13–24 are Cl, Br, and I for UCC, UBC, and UIC, respectively and atoms 13–17 are H and 18–24 are Br for HBC.

Charge delocalization allows for weaker interactions to occur at sites along the periphery of the anion. Natural population analysis (NPA) is one computational method that allows the charge density of a molecule to be partitioned among the various atomic nuclei. NPA was selected over Mulliken population analysis because Mulliken values are highly dependent on the basis set used (69–71). The NPA values calculated for the halogenated carboranes are found in Table 8 (for atomic numbering scheme refer to FIG. 7).

TABLE 8

| UC[a] | | | UCC | | | UBC | | | UIC | | | HBC | | |
|---|---|---|---|---|---|---|---|---|---|---|---|---|---|---|
| Atom | # | Charge | Atom | # | Charge | Atom | # | Charge | Atom | # | Charge | Atom | # | Charge |
| CH | 1 | −0.39 | C | 1 | −0.8019 | C | 1 | −0.7922 | C | 1 | −0.7573 | C | 1 | −0.7717 |
| BH | 2 | −0.11 | B | 2 | −0.0060 | B | 2 | −0.1303 | B | 2 | −0.2959 | B | 2 | −0.1111 |
| BH | 3 | 0.03 | B | 3 | 0.1332 | B | 3 | 0.0259 | B | 3 | −0.1697 | B | 3 | 0.0408 |
| BH | 4 | 0.03 | B | 4 | 0.1332 | B | 4 | 0.0259 | B | 4 | −0.1685 | B | 4 | 0.0408 |
| BH | 5 | 0.03 | B | 5 | 0.1332 | B | 5 | 0.0259 | B | 5 | −0.1670 | B | 5 | 0.0408 |
| BH | 6 | 0.03 | B | 6 | 0.1332 | B | 6 | 0.0259 | B | 6 | −0.1685 | B | 6 | 0.0408 |
| BH | 7 | 0.03 | B | 7 | 0.1332 | B | 7 | 0.0259 | B | 7 | −0.1967 | B | 7 | 0.0408 |
| BH | 8 | −0.13 | B | 8 | −0.0254 | B | 8 | −0.1332 | B | 8 | −0.3278 | B | 8 | −0.1390 |
| BH | 9 | −0.13 | B | 9 | −0.0254 | B | 9 | −0.1332 | B | 9 | −0.3313 | B | 9 | −0.1390 |
| BH | 10 | −0.13 | B | 10 | −0.0254 | B | 10 | −0.1332 | B | 10 | −0.3295 | B | 10 | −0.1390 |
| BH | 11 | −0.13 | B | 11 | −0.0254 | B | 11 | −0.1332 | B | 11 | −0.3295 | B | 11 | −0.1390 |
| BH | 12 | −0.13 | B | 12 | −0.0254 | B | 12 | −0.1332 | B | 12 | −0.3313 | B | 12 | −0.1390 |
| | | | H | 13 | 0.3589 | H | 13 | 0.3541 | H | 13 | 0.3596 | H | 13 | 0.3276 |
| | | | Cl | 14 | −0.1053 | Br | 14 | 0.0008 | I | 14 | 0.1917 | Br | 14 | −0.0170 |
| | | | Cl | 15 | −0.0945 | Br | 15 | 0.0124 | I | 15 | 0.2038 | Br | 15 | −0.2067 |
| | | | Cl | 16 | −0.0945 | Br | 16 | 0.0124 | I | 16 | 0.2035 | Br | 16 | −0.2067 |
| | | | Cl | 17 | −0.0945 | Br | 17 | 0.0124 | I | 17 | 0.2059 | Br | 17 | −0.2067 |
| | | | Cl | 18 | −0.0945 | Br | 18 | 0.0124 | I | 18 | 0.2035 | Br | 18 | −0.2067 |
| | | | Cl | 19 | −0.0945 | Br | 19 | 0.0124 | I | 19 | 0.2038 | Br | 19 | −0.2067 |
| | | | Cl | 20 | −0.1025 | Br | 20 | 0.0029 | I | 20 | 0.1955 | H | 20 | 0.0393 |
| | | | Cl | 21 | −0.1025 | Br | 21 | 0.0029 | I | 21 | 0.1954 | H | 21 | 0.0393 |
| | | | Cl | 22 | −0.1025 | Br | 22 | 0.0029 | I | 22 | 0.1943 | H | 22 | 0.0393 |
| | | | Cl | 23 | −0.1025 | Br | 23 | 0.0029 | I | 23 | 0.1940 | H | 23 | 0.0393 |
| | | | Cl | 24 | −0.1025 | Br | 24 | 0.0029 | I | 24 | 0.1954 | H | 24 | 0.0393 |

[a]UC = Unsubstituted carborane ($CB_{11}H_{12}$).
Calculated at the B3LYP/6–31 G(d) level (Reference 85)

There are several criteria that must be satisfied in order for a prospective ion-exchanger to become routinely used in ion-selective chemical sensors. Some of the more important characteristics that need to be exhibited include the presence of a low, delocalized charge (so that the electrostatic interactions are minimized), sufficient lipophilicity and chemical stability, and preservation of electrode response characteristics, such as sensitivity and selectivity.

Thus, several halogenated carborane anions (see FIG. 7) were evaluated as suitable ion-exchangers for ion-selective sensors. Ion coordination ability, chemical stability in acid and/or lipophilicity, and response characteristics (slope and selectivity) were used as criteria. The segmented sandwich There are primarily four distinct regions of charge density for each icosahedral carborane. With reference to FIG. 1, these four regions are (1) C1, (2) B2, which is the boron atom opposite to C1 (also referred to as the antipodal position), (3) B3–B7, which denotes the upper pentagonal belt, and (4) B8–B12, which is the lower pentagonal belt. Atom number 14 refers to the halogen attached to the antipodal boron atom, while atoms 15–19 and 20–24 refer to the substituents attached to each boron atom on the lower and upper pentagonal belts, respectively.

Interestingly, the lower pentagonal belt possesses more negative charge than the upper belt (both boron atoms and substituents alike). This trend holds for all of the halogenated carboranes as well as for the unsubstituted parent ion (UC). It is also apparent that the substitution of halogens that are less electron-withdrawing decreases the charge density on the periphery of the anion, thus shielding the charge located on the boron atoms. This would indicate a more weakly coordinating species, which is favorable in ISEs because it prevents the ion-exchanger from interacting with extracted cations, which is sometimes seen with some of the tetraphenylborate anions (i.e., through π-interactions) (48).

It was also surprising that the overall charge magnitude obtained for each boron and its substituent are nearly identical for each of the carboranes. For example, if one sums the charge density for the antipodal boron (B2) and its substituent (R14), the overall charge is approximately −0.1 for all of the halogenated carboranes as well as for the unsubstituted parent anion (89). This indicates that the amount of charge density for a given atom location on the cage (i.e. boron+substituent) is always the same. The distribution of charge, however, is different depending on the partitioning imparted by the substituents electron-withdrawing ability. Thus, it should be possible to create numerous anions with a variety of coordination abilities and lipophilicities. Furthermore, the susceptibility of carboranes to electrophilic substitution is an inherent advantage that may be exploited for the development of a wide variety of ion-exchangers with tailored lipophilicities.

Another trend that is apparent is the increased amount of charge density on the halogen (X14) bound to the antipodal boron relative to the other substituents of the lower belt. It is this position that is the most susceptible to electrophilic attack. One would expect that this location would most likely be involved in weak electrostatic interactions within ISE membranes. It is also noteworthy that the effective dipole moment decreases as the ionic radius of the halogen increases. The calculated dipole moments are 2.67, 2.20, and 2.01 D for UCC, UBC, and UIC, respectively. This may also be a parameter affecting the relative interactions of these anions. The presence of weakly basic sites (i.e., halogens or hydrogen) is also advantageous because it reduces the coordination ability of the anion. Of the isostructural carboranes studied it appears that UIC may be the best choice based on its superior charge delocalization.

HBC is used as a comparative standard for the undecahalogenated carboranes because it is the most lipophilic carborane anion that is commercially available. Interestingly, HBC seems to be strikingly similar to UCC in terms of charge density distribution. However, its effective dipole moment is 0.07 D, which is somewhat counterintuitive when one considers the physical constitution of this molecule.

Another computational tool that can be used to predict the coordination behavior of the carborane ion-exchangers is an electrostatic map. The electrostatic map is a plot of the electrostatic potential (EP) at a fixed electron density. Often, electrostatic maps are used to predict where electrophilic attack is most likely to occur (86). The electrostatic potential can be defined as the work done to bring unit positive charge from infinity to a point. Unlike electron density, the EP contains contributions from both the nuclei and the electrons. The electrostatic interaction energies can be visualized in the same manner as charge densities because the EP varies through space.

Electrostatic maps were calculated for UCC, UBC, and HBC (data not shown). Limitations of the Spartan® program did not allow for the calculation of an electrostatic map for UIC. The data corresponded well with the charge density data for the antipodal units in Table 8. Knowing the calculated interaction energies it is possible to determine a trend for the strength of the ion-exchanger interactions. The interaction energies for UBC, UCC, and HBC, are 54, 64, and 60 kcal/mol, respectively. This means that the order of binding strength is UCC>HBC>UBC. This data validates the prediction that HBC would behave similarly to UCC. Moreover, had it been possible to generate an electrostatic contour for UIC, it is probable that it would appear after UBC in the series and it should possess an interaction energy of less than 54 kcal/mol.

The computational study, which gave some predication of the degree of electrostatic interactions of the carboranes, was compared to potentiometric data evaluating their ion pairing ability. A method that has seen increasing utility in determining interactions within ISE membranes is the segmented sandwich technique. The sandwich technique was adapted herein to determine ion-pairing interactions relative to the best tetraphenylborate, TFPB.

For this study, single membrane potentials were determined for membranes containing either TFPB or a triammonium salt of the carboranes UBC, UCC, HBC, and UIC. Then, the membranes were fused together with the TFPB-containing membrane in contact with the inner solution and the carborane-containing membrane in contact with the sample. The potential generated from this configuration is dependent on the interaction of the carborane anion with the sample cations. By subtracting the average single membrane potentials from the average sandwiched membrane potentials it is possible to determine a ΔEMF value that indicates the degree to which a carborane anion has interacted with a sample cation relative to the binding behavior of TFPB. The EMF values obtained for the carboranes in DOS and o-NPOE-plasticized membranes are found in Table 10.

It is apparent from the data in Table 10 that UIC forms the weakest ion pairs relative to the other halogenated carboranes, however, the positive charge sign indicates a stronger interaction than exhibited by TFPB. For binding studies with $K^+$, the effect of the plasticizer polarity was minimal. Conversely, for $Ca^{2+}$ binding studies, stronger interactions occurred in the more polar o-NPOE plasticizer. It is noteworthy to mention that a Nernstian cationic slope was confirmed for each membrane segment in both plasticizers studied. The results of the binding studies conclusively establish that UIC interacts minimally with cations relative to the other carborane anions. These results confirm the predicted interactions of the computational data found in Tables 8 and 9. The sandwich method also clarified the relative position of HBC, which binds comparably to UCC, which was also predicted by computation. The relative sequence of binding strength for $K^+$ is HBC≈UCC>UBC≈UIC. On the other hand, the binding sequence towards $Ca^{2+}$ shows larger differences in binding affinity: HBC>UCC>UBC>UIC.

TABLE 9

Response slopes[a] and unbiased selectivity coefficients[b] of PVC-DOS ISEs containing Pb$^{2+}$ ionophore IV and an ion-exchanger.

| | TFPB | | UIC | | UBC | | UCC | | HBC | |
|---|---|---|---|---|---|---|---|---|---|---|
| Ion | Slope | $K^{pot}_{Pb,J}$ | Slope | $K^{pot}_{Pb,J}$ | Slope | $K^{pot}_{Pb,J}$ | Slope | $K^{pot}_{Pb,J}$ | Slope | $K^{pot}_{Pb,J}$ |
| Pb$^{2+}$ | 30.58 ± 0.61 | 0 | 28.95[c] ± 0.89 | 0 | 28.48 ± 2.44 | 0 | 33.72 ± 1.37 | 0 | 27.11 ± 0.93 | 0 |
| Ca$^{2+}$ | 27.49 ± 0.73 | −13.75 ± 0.14 | 20.11 ± 1.15 | −14.55 ± 0.10 | 19.68 ± 2.92 | −13.81 ± 0.12 | 11.31 ± 0.81 | −13.70 ± 0.33 | 10.39 ± 3.38 | −13.08 ± 0.51 |
| Na$^{+}$ | 59.72 ± 0.18 | −7.24 ± 0.06 | 55.34 ± 0.42 | −7.39 ± 0.04 | 53.65 ± 0.16 | −7.58 ± 0.13 | 52.71 ± 0.56 | −7.30 ± 0.27 | 51.04 ± 0.39 | −6.38 ± 0.16 |
| Cd$^{2+}$ | 31.22 ± 0.11 | −6.42 ± 0.07 | 29.87 ± 0.21 | −7.97 ± 0.05 | 29.10 ± 0.15 | −7.80 ± 0.12 | 28.57 ± 1.18 | −6.79 ± 0.25 | 26.12 ± 0.78 | −6.72 ± 0.11 |
| Cu$^{2+}$ | 33.98 ± 0.44 | −3.89 ± 0.15 | 35.14 ± 1.24 | −3.06 ± 0.17 | 34.89 ± 0.76 | −3.29 ± 0.21 | 41.64 ± 1.12 | −3.32 ± 0.17 | 38.58 ± 0.97 | −2.73 ± 0.16 |

[a]Mean vaules of five electrodes. Slope is in mV per decade.
[b]SMM; Mean values calculated using experimental values from $10^{-1}$–$10^{-4}$ M
[c]Calculated using experimental values from $10^{-2}$–$10^{-4}$ M.

TABLE 10

Potentiometric evaluation of ion-pairing ability for carborane ion-exchangers relative to the binding behavior of TFPB.

| | K$^{+}$ | | Ca$^{2+}$ | |
|---|---|---|---|---|
| Anion | DOS ΔEMF | NPOE ΔEMF | DOS ΔEMF | NPOE ΔEMF |
| UIC | 13.4 ± 0.2 | 11.6 ± 0.6 | 22.9 ± 0.1 | 47.9 ± 0.6 |
| UBC | 13.3 ± 0.2 | 10.1 ± 0.7 | 31.2 ± 0.4 | 60.4 ± 0.7 |
| UCC | 18.1 ± 0.5 | 19.3 ± 0.6 | 34.6 ± 0.7 | 72.3 ± 0.6 |
| HBC | 20.1 ± 0.9 | 22.6 ± 1.1 | 39.2 ± 0.7 | 78.7 ± 0.6 |

In addition to charge delocalization, there are other characteristics that an ion-exchanger must possess in order to be useful for use in ion-selective sensors. One parameter that affects the lifetime of sensing devices is the lipophilicity of the active components. It is known that carboranes are resistant to acid and may be easily functionalized with lipophilic groups. Facile solid-state synthetic routes are now available that produce single products in yields as high as 90%, thus allowing various derivatives to be synthesized (60).

In order to compare the relative stability/lipophilicity of the halogenated carborane anions to TFPB, thin films approximately 2 μm in diameter were fashioned using DOS plasticized PVC that contained equimolar amounts of a halogenated carborane ion-exchanger and a chromoionophore with an acidic pK$_a$ value, ETH 5315 (pK$_a$ (DOS)= 4.9±0.03). [The pK$_a$ of the chromoionophore was determined in situ using the segmented sandwich membrane technique. The value found here agrees nicely with the value of 5.2, which was previously obtained indirectly via optical and potentiometric experiments (87)]. The films were equilibrated in a flow cell that contained 0.2 M HOAc as previously described, and the acid was continuously replaced at a rate of 1.2 mL/min.

Figure 8:
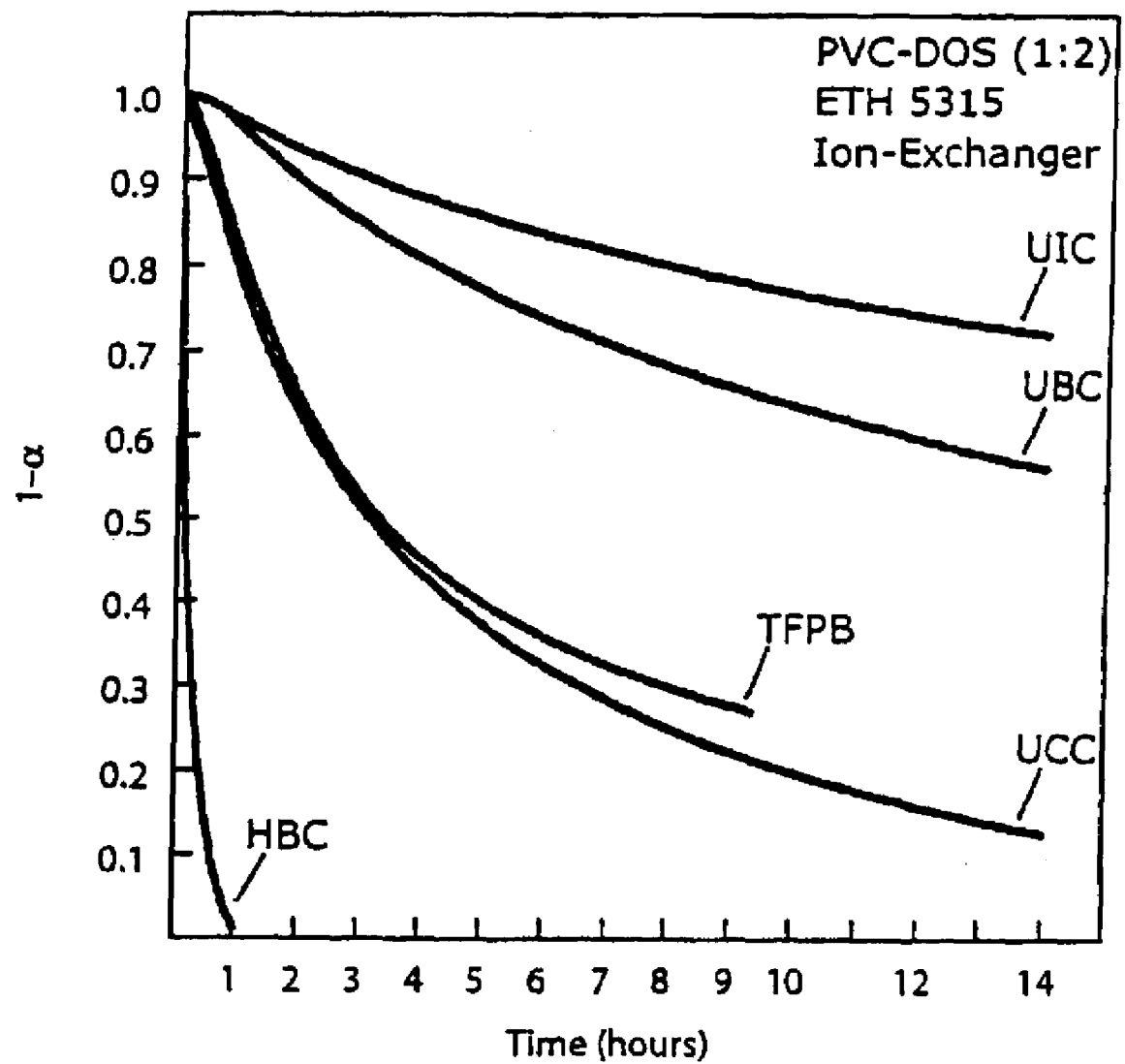
FIG. 8 is a graph of the chemical stability and/or lipophilicity of TFPB and halogenated carborane anions HBC, UCC, UBC, and UIC in the presence of 0.2 M HOAc under flowing conditions. The ordinate values (1-α) are the mole fraction of protonated chromoionophore.

FIG. 8 is a graph illustrating the chemical stability and/or lipophilicity of TFPB and halogenated carborane anions HBC, UCC, UBC, and UIC in the presence of 0.2 M HOAc under flowing conditions. The leaching behavior of TFPB and the carboranes appears as FIG. 8. Because of the resilience of carboranes in acid it is plausible that the primary mechanism affecting leaching behavior is insufficient lipophilicity. For TFPB, on the other hand, both acid hydrolysis and lipophilicity are contributing factors. As shown in FIG. 8, both UBC and UIC are substantially better than TFPB under flowing acidic conditions, however, due to the noticeable decrease it is necessary for further developments to be made, either through the creation of new derivatives or through covalent modification of existing carboranes. Both the leaching behavior of UBC and TFPB are reasonably comparable to work previously reported, taking into consideration the experimental modifications (i.e., flowing mode vs. static) (88). Furthermore, it is evident that HBC is not a good choice due to its undesirable retention time. It is known that hexahalogenated carboranes are much more stable in acid than tetraphenylborates (89), therefore the loss of HBC from the film is primarily due to insufficient lipophilicity. Surprisingly, the behavior of UCC is very similar to that of TFPB. From the leaching data depicted in FIG. 8, once again it appears that UIC is the most favorable carborane of those studied.

Figure 9B:
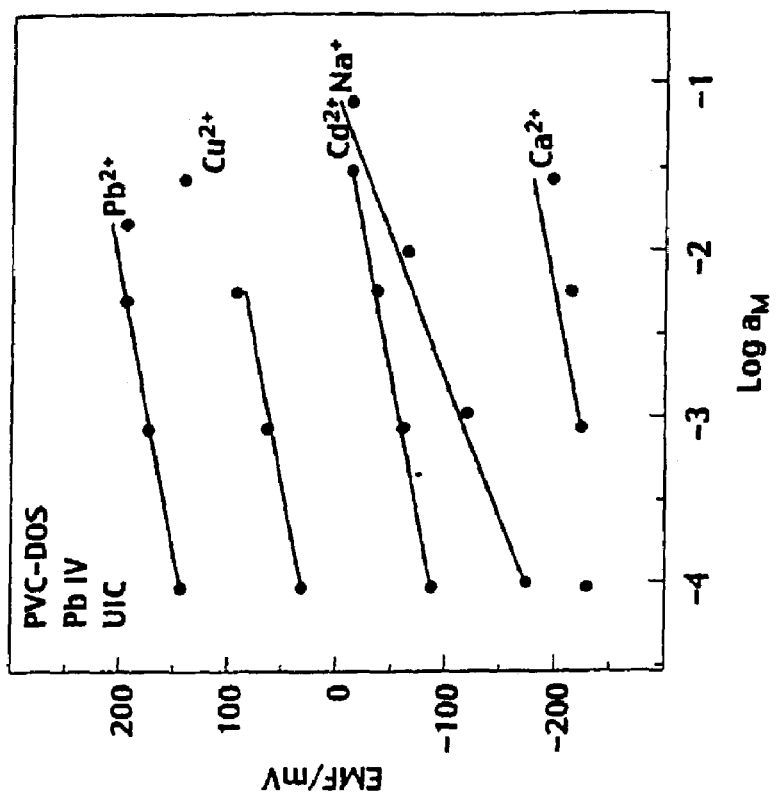
FIGS. 9A and 9B are graphs of the response behavior of PVC-DOS ISE membranes containing Pb-IV and either TFPB (9A) or UIC (9B). Solid lines denote Nernstian response slopes for each ion.
Figure 9A:
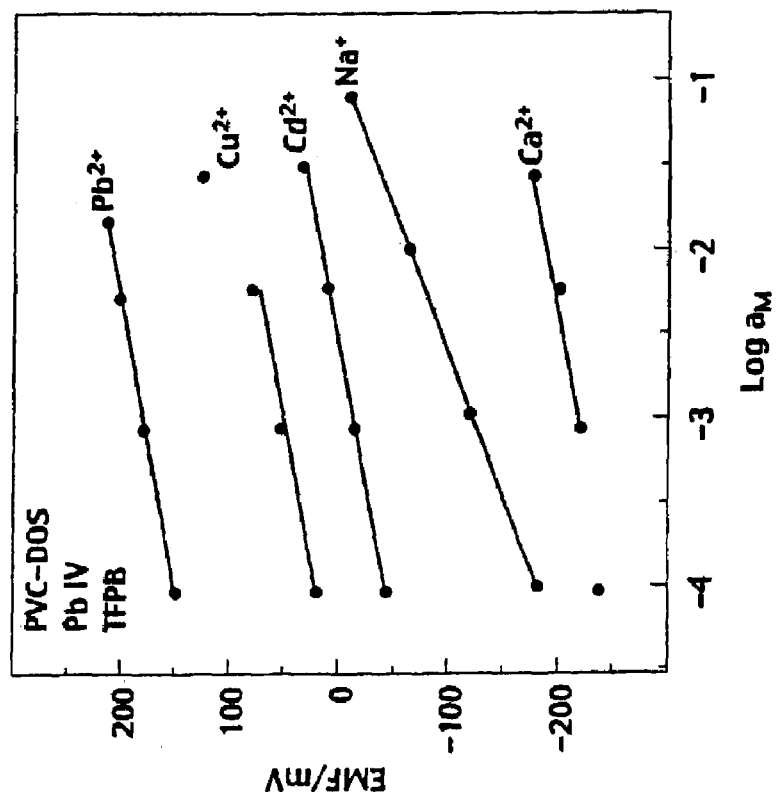

In order to evaluate the functionality of the carboranes, ISEs were prepared containing a Pb$^{2+}$-selective ionophore (Lead IV), which is a calix[4]arene derivative. The electrodes were evaluated in terms of response behavior and selectivity. The data obtained are shown in Table 10 as the mean of five electrodes. From the data it is apparent that all of the carboranes give a Nernstian response towards lead ions. However, for UCC and HBC the selectivity is less than desirable. Both UBC and UIC appear to be quite comparable to TFPB, with only slight deviations from Nernstian behavior. FIGS. 9A and 9B compare the calibration curves for TFPB and UIC, respectively. Of interest, UIC and UBC both show a marked improvement in the discrimination of Cd$^{2+}$ by nearly 1.5 orders of magnitude, meanwhile exhibiting a decreased selectivity of nearly 0.8 orders for Cu$^{2+}$. It should be noted that the selectivity values reported here for the system containing TFPB match quite well with previously published work (62).

In addition to differences in selectivity, UIC also showed promise for improving detection limits. Calibration curves for UIC and TFPB were extrapolated to the baseline potential of the electrodes in water prior to measurement of the primary ion, which allowed for a crude approximation of the detection limit. It should be mentioned that this comparison was merely qualitative due to the super-Nernstian response of the electrodes for lead ions at lower sample activities. This was expected because of the constitution of the IFS (0.01 M NaCl). For TFPB, the estimated detection limit was −12.97±0.32, while for UIC it was estimated to be −16.36±0.85 (data not shown). Interestingly, UIC was the only carborane that exhibited this behavior. This result suggests that UIC may be suitable for the realization of ion-selective electrodes with even lower detection limits than what is currently possible.

CONCLUSION

It has been shown herein that MMA-DMA is a suitable parent matrix for preparing plasticizer-free polymers with grafted ionophores. Covalent grafting of hydrophilic crown ether-type ionophores illustrated an improvement in sensor sensitivity and selectivity relative to membranes containing entrapped ionophores.

It has also been shown herein for the first time that derivatives of 3-oxapentanediamide-type calcium ionophores comprising a polymerizable group can effectively be immobilized in MMA-DMA, while maintaining Nernstian response slopes for calcium ions and a relatively high selectivity. Time dependent sandwich membrane experiments confirmed the drastically reduced mobility of the grafted ionophore in MMA-DMA. This marks the first time that the sandwich membrane technique was used to study covalently immobilized ionophores. The first hydrophobia bulk optodes containing a grafted calcium ion-selective ionophore and no plasticizer were prepared using MMA-DMA-AU-1 and exhibited a functional calcium ion response according to classical optode theory. The selectivity observed over common interferents such as $Na^+$, $K^+$, and Mg was high, and encouraging for future development. Optode response times decreased drastically if the grafted polymer was blended with PVC-DOS, and the response range was, for the first time, found to be adequate for physiological assessment of calcium at neutral pH.

Halogenated carboranes offer numerous advantages that may be exploited in ionophore-based sensing platforms. Of the carborane derivatives studied, UIC demonstrated the weakest interactions in both polar and apolar membrane solvents for $K^+$ and $Ca^{2+}$ as determined using the segmented sandwich membrane technique. Surprisingly, UIC showed a marked improvement in selectivity and a lower detection limit relative to TFPB. This unexpected discovery will be very useful in the development of ion-exchangers for creating sensors with improved lifetimes and characteristics, such as selectivity.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes, which come within the meaning and range of the equivalence of the claims, are to be embraced within their scope.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

REFERENCES (1) Schefer, U.; Ammann, D.; Pretsch, E.; Oesch, U.; Simon, W. *Anal. Chem.* 1986, 55, 2282.
(2) Simon, W.; Carafoli, E. *Meth. Enzymology* 1979, LV1 439.
(3) Bakker, E. *Anal. Chem.* 1997, 69, 1061.
(4) Rosatzin, T.; Andersson, L. L; Simon, W.; Mosbach, K. *J. Chem. Soc. Perkin Trans.* 1992, 2, 1261.
(5) Song, A.; Parus, S.; Kopelman, R. *Anal. Chem.* 1997, 69, 863–867.
(6) Barker, S. L. R.; Thorsrud, B. A.; Kopelman, R. *Anal. Chem.* 1998, 70, 100–104.
(7) Shortreed, M.; Bakker, E.; Kopelman, R. *Anal. Chem.* 1996, 68, 2656–2662.
(8) Shortreed, M. R.; Dourado, S.; Kopelman, R. *Sens. Actuat. B* 1997, 38–39, 8–12.
(9) Brasuel, M.; Kopelman, R.; Miller, T. J.; Tjalkens, R.; Philbert, M. A. *Anal. Chem.* 2001, 73, 2221–2228.
(10) Peper, S.; Tsagkatakis, I.; Bakker, E. *Anal. Chim. Acta* 2001, 442, 25–33.
(11) Tsagkatakis, I.; Peper, S.; Bakker, E. *Anal. Chem.* 2001, 73, 315–320.
(12) Tsagkatakis, I.; Peper, S.; Retter, R.; Bell, M.; Bakker, E. *Anal. Chem.* 2001, 73, 6083–6087.
(13) Retter, R.; Peper, S.; Bell, M.; Tsagkatakis, I.; Bakker, E. *Anal. Chem.,* 2002, 74, 5420–5425.
(14) Clark, H. A.; Kopelman, R.; Tjalkens, R.; Philbert, M. A. *Anal. Chem.* 1999, 71, 4837–4843.
(15) Morf, W. E.; Seiler, K.; Sorensen, P. R.; Simon, W., *Proceedings of the Fifth Symposium on Ion-Selective Electrodes*, Matrafured, Hungary 1988; Akademiai Kiado; 141–152.
(16) Eugster, R.; Rosatzin, T.; Rusterholz, B.; Aebersold, B.; Pedrazza, U.; Ruegg, D.; Schmid, A.; Spichiger, U. E.; Simon, W. *Anal. Chim. Acta* 1994, 289, 1–13.
(17) Moody, G. J. In *Biosensors & Chemical Sensors;* Edelman, P. G., Wang, J., Eds.; American Chemical Society: Washington, D.C., 1992; Vol. ACS Symposium Series 487, pp 99–110.
(18) Reinhoudt, D. N.; Engbersen, J. F. J.; Brzozka, Z. *Anal. Chem.* 1994, 66, 3618.
(19) Lindner, E.; Cosofret, V. V.; Ufer, S.; Johnson, T. A.; Ash, R. B.; Nagle, H. T.; Neuman, M. R.; Buck, R. P. Fr. J. *Anal. Chem.* 1993, 346, 584.
(20) Yun, S. Y.; Hong, Y. K.; Oh, B. K.; Cha, G. S.; Nam, H.; Lee, S. B.; Jin. J.-I. *Anal. Chem.* 1997, 69, 868–873.
(21) Lindner, E.; Niegreisz, Z.; Toth, K.; Pungor, E.; Berube, T. R.; Buck, R. P. *J. Electroanal. Chem.* 1989, 259, 67–80.
(22) Yoon, I. J.; Lee, D. K.; Nam, H.; Cha, G. S.; Strong, T. D.; Brown, R. B. *J. Electroanal. Chem.* 1999, 464, 135–142.
(23) Bobacka, J.; Ivaska, A.; Lewenstam, A. *Anal. Chim. Acta* 1999, 385, 195–202.
(24) Dimitrakopoulos, T.; Farrell, J. R.; lies, P. J. *Electroanalysis* 1996, 8, 391–395.
(25) Qin, Y.; Peper, S.; Bakker, E. *Electroanalysis* 2002, 14, 1375.
(26) Heng, L. Y.; Hall, E. A. H. *Anal. Chem.* 2000, 72, 42–51.
(27) Malinowska, E.; Gawart, L.; Parzuchowski, P.; Rokicki, G.; Brzozka, Z. *Anal. Chim. Acta* 2000, 421, 93–101.
(28) Horn, M. B. *Acrylic Resins,* Reinhold Publishing Corp., New York 1960.
(29) L. Y. Heng, E. A. H. Hall, *Anal. Chem. Acta* 2001, 443, 25.
(30) Puntener, M.; Fibbioli, M.; Bakker, E.; Pretsch, E. *Electroanalysis* 2002, 14, 1329.
(31) Kimura, K.; Sunagawa, T.; Yajima, S.; Miyake, S.; Yokoyama, M. *Anal Chem.* 1998, 70, 4309.
(32) Ebdon, L.; Ellis, A. T.; Corfield, G. C. *Analyst* 1979, 104, 730.
(33) Daunert, S.; Bachas, L. G. *Anal.Chem.* 1990, 62, 1428.

(34) Cross, G. G.; Fyles, T. M. *Talanta* 1994, 41, 1589.
(35) Heng, L. Y.; Hall, E. A. H. *Electroanalysis* 2000, 12, 178.
(36) Rosatzin, T.; Holy, P.; Seiler, K.; Rusterholz, B.; Simon, W. *Anal Chem* 1992, 64, 2029.
(37) Morf, W. E.; Seiler, K.; Rusterholz, B.; Simon, W. *Anal. Chem.* 1990, 62, 738.
(38) Steinke, J.; Shenington, D. C.; Dunkin, I. R. *Adv. Polym. Sci.* 1995, 123, 81–125.
(39) Haupt, K. *Analyst* 2001, 725, 747–756.
(40) Perez, N.; Whitcombe, M. J.; Vulfson, E. N. *Macromolecules* 2001, 34, 830.
(41) Ye, L.; Cormack, P. A. G.; Mosbach, K. *Anal. Commun.* 1999, 36, 35.
(42) Ye, L.; Weiss, R.; Mosbach, K. *Macromolecules* 2000, 33, 8239.
(43) Piletsky, S. A.; Turner, A. P. F. *Electroanalysis* 2002, 14, 317–323.
(44) Qin, Y.; Peper, S.; Bakker, E. *Anal.Chem.* 2002, Submitted.
(45) Bakker, E.; Pretsch, E. *Anal. Chim. Acta* 1995, 309, 7.
(46) Bakker, E.; Buhlmann, P.; Pretsch, E. *Chem. Rev.* 1997, 97, 3083–3132.
(47) Rosatzin, T.; Bakker, E.; Suzuki, K.; Simon, W. *Anal. Chim. Acta* 1993, 280, 197.
(48) Strauss, S. *Chem. Rev.* 1993, 93, 927.
(49) Nishida, H.; Takada, N.; Yoshimura, M.; Sonoda, T.; Kobayashi, H. *Bull. Chem. Soc. Jpn.* 1984, 75, 2600.
(50) Ceresa, A.; Bakker, E.; Hattendorf, B.; Günther, D.; Pretsch, E. *Anal. Chem.* 2001, 72, 343.
(51) Reed, C. *Acc. Chem. Res.* 1998, 31, 133.
(52) Tsang, C.-W.; Xie, Z. *Chem. Comm.* 2000, 1839.
(53) Jelinek, T.; Baldwin, P.; Scheidt, W. R.; Reed, C. A. *Inorg. Chem.* 1993, 32, 1982.
(54) Xie, Z.; Tsang, C.-W.; Xue, F.; Mak, T. C. W. *J. Organometallic Chem.* 1999, 577, 197.
(55) Xie, Z.; Tsang, C.-W.; Sze, E. T.-P.; Yang, Q.; Chan, D. T. W.; Mak, T. C. W. *Inorg. Chem.* 1998, 37, 6444.
(56) Sandier, S. R.; Karo, W. *Polymer Synthesis: 2nd ed.*; Academic Press: San Diego, Calif., 1992; Vol. 1.
(57) Mi, Y.; Bakker, E. *Anal. Chem.* 1999, 71, 5279.
(58) Qin, Y.; Mi, Y.; Bakker, E. *Anal. Chim. Acta.* 2000, 421, 207.
(59) Seiler, K.; Simon, W. *Anal. Chim. Acta* 1992, 266, 73.
(60) Xie, Z.; Tsang, C.-W.; Sze, E. T.-P.; Yang, Q.; Chan, D. T. W.; Mak, T. C. W. *Inorg. Chem.* 1998, 37, 6444.
(61) Mi, Y.; Bakker, E. *Electrochem. Solid State Lett.* 2000, 3, 159.
(62) Ceresa, A.; Pretsch, E. *Anal. Chim. Acta.* 1999, 395, 41.
(63) Bakker, E.; Pretsch, E.; Buhlmann, P. *Anal. Chem.* 2000, 72, 1127.
(64) Bakker, E.; Buhlmann, P.; Pretsch, E. *Electroanalysis* 1999, 11, 915.
(65) Bakker, E. *J. Electrochem. Soc.* 1996, 143, L83.
(66) Meier, P. C. *Anal. Chim. Acta* 1982, 136, 363.
(67) Dewar, M. J. S.; Zoebisch, E. G.; Healy, E. F. *J. Am. Chem. Soc.* 1985, 107, 3902.
(68) Spartan, Wavefuntion, Inc.: Irvine, Calif.
(69) Reed, A. E.; Weinstock, R. B.; Weinhold, F. *J. Chem. Phys.* 1985, 83, 735.
(70) Reed, A.; Curtiss, L. A.; Weinhold, F. *Chem. Rev.* 1988, 88, 899.
(71) Weinhold, F. A. In *Encyclopedia of Computational Chemistry*; Schleyer, P. v. R., Ed.; Wiley Publishers: New York, 1998; Vol.3, pp 1792.
(72) Schefer, U.; Ammann, D.; Pretsch, E.; Oesch, U.; Simon, W. *Anal. Chem.* 1986, 58, 2282.
(73) Shultz, M. M.; Stefanova, 0. K.; Mokrov, S. B.; Mikhelson, K. N. *Anal. Chem*, 2002, 74, 510.
(74) Bakker, E.; Xu, A.; Pretsch, E. *Anal. Chim. Acta.* 1994, 295, 253.
(75) Ku, C. C.; Liepins, R. *Electrical Properties of Polymers*; New York, 1987.
(76) Lee, M. H.; Yoo, C. L.; Lee, J. S.; Cho, I.-S.; Kim, B. H.; Cha, G. S.; Nam, H. *Anal Chem.* 2002, 74, 2603.
(77) Peper, S.; Ceresa, A.; Qin, Y.; Bakker, E. 2003, 500, in press.
(78) Bakker, E.; Simon, W. *Anal Chem.* 1992, 64, 1805.
(79) Bakker, E. *Anal. Chim. Acta* 1997, 350, 329.
(80) Wulff, G.; Vietmeier, T.; Poll, H.-G. *Makromol. Chem.* 1987, 755, 731–40.
(81) Wulff, G.; Minarik, M. *J.Liq. Chrom* 1990, 13, 2987–3001.
(82) Wulff, G.; Vesper, W. *J. Chrom.* 1978, 167, 171–86.
(83) Jain, A. K.; Gupta, V. K.; Singh, R. D.; Khurana, U.; Singh, L. P. *Sens. Actuators B* 1997, 40, 15–20.
(84) Buhlmann, P.; Pretsch, E.; Bakker, E. *Chem. Rev.* 1998, 98, 1593–1687.
(85) McKee, M. L. *J. Am. Chem. Soc.* 1997, 119, 4220.
(86) Leach, A. R. *Molecular Modelling: Principles and Applications*, 2nd ed.; Prentice Hall: London, 2001.
(87) Sokalski, T. et al., *Anal. Chem.* 1999, 71, 1210.
(88) Peper, S.; Telting-Diaz, M.; Almond, P.; Albrecht-Schmitt, T.; Bakker, E. *Anal. Chem.* 2002, 74, 1327.
(89) Reed, E. *Ace. Chem. Res.*, 1998, 31, 133.
(90) Lerchi, M.; Bakker, E.; Rusterholz, B.; Simon, W. *Anal. Chem.* 1992, 64, 1534.

What is claimed is:

1. An ion-detecting sensor for detecting a target ion in a sample, comprising (i) a self-plasticizing copolymer comprising polymerized units of methacrylate monomers; and (ii) a functionalized ionophore of said ion, wherein at least a portion of the functionalized ionophore is grafted onto the copolymer through covalent linkages, and wherein said methacrylate monomers comprise a monomer having an $R_1$ pendant alkyl group and a monomer having an $R_2$ pendant alkyl group, wherein $R_1$ is any of $C_{1-3}$ alkyl groups and $R_2$ is any of $C_{4-12}$ alkyl groups, wherein the self-plasticizing copolymer has a glass transitional temperature ($T_g$) of about or below 0° C.

2. The ion-detecting sensor of claim 1, wherein said ionophore is a derivative of a 3-oxapentandiaminde-type calcium ionophore, said derivative comprising a polymerizable moiety.

3. The ion-detecting sensor of claim 1, wherein said ionophore is a hydrophilic crown ether.

4. The ion-detecting sensor of claim 3, wherein said crown ether is 4'-acryloylamidobenzo-15-crown-5.

5. The ion-detecting sensor of claim 3, wherein said crown ether is 4'-acyloylamidobenzo-18-crown-6.

6. The ion-detecting sensor of claim 1, wherein $R_1$ is any of $C_{1-2}$ alkyl groups and $R_2$ is any of $C_{8-12}$ alkyl groups.

7. The ion-detecting sensor of claim 1, wherein $R_1$ is a $C_1$ alkyl group, and $R_2$ is a $C_{10}$ alkyl group.

8. The ion-detecting sensor of claim 1, wherein the polymer is in a form of membrane.

9. The ion-detecting sensor of claim 8, wherein the self-plasticizing ion-detecting sensor is a carrier-based ion-selective electrode.

10. The ion-detecting sensor of claim 8, wherein the self-plasticizing copolymer and functionalized ionophore forms a thin film ion-specific optode.

11. The ion-detecting sensor of claim 8, wherein the self-plasticizing copolymer and functionalized ionophore forms a bulk optode.

12. The ion-detecting sensor of claim 1, wherein the polymer is in a form of particles.

13. The ion-detecting sensor of claim 12, wherein the self-plasticizing copolymer and functionalized ionophore forms a particle-based optode.

14. The ion-detecting sensor of claim 1, further comprising an indicator ionophore.

15. The ion-detecting sensor of claim 1, further comprising an ion exchanger.

16. The ion-detecting sensor of claim 15, wherein the ion exchanger is a salt of a halogenated carborane anion.

17. The ion-detecting sensor of claim 16, wherein the halogenated carborane anion is 2, 3, 4, 5, 6, 7, 8, 9, 10, 11, 12 undecabromocarborane, undecachlorinatedcarborane, hexabrominatedcarborane and undecaiodinatedcarborane.

18. The ion-detecting sensor of claim 16, wherein the ion exchanger is trimethylammonium undecaiodinatedcarborane.

19. The ion-detecting sensor of claim 1, comprising a sample, wherein the sample is a body fluid selected from the group consisting of whole blood, spinal fluid, blood serum, urine, saliva, semen, and tears.

20. The ion-detecting sensor of claim 1, wherein said copolymer is blended with poly(vinyl chloride) and a plasticizer.

21. An ion-detecting sensor for detecting a target ion in a sample, comprising (i) a self-plasticizing copolymer comprising polymerized units of methacrylate monomers; and (ii) a functionalized ionophore of said ion, wherein at least a portion of the functionalized ionophore is grafted onto the copolymer through covalent linkages, and wherein said methacrylate monomers have an $R_1$ or $R_2$ pendant alkyl groups wherein $R_1$ is any of $C_{1-3}$ alkyl groups and $R_2$ is any of $C_{4-12}$ alkyl groups, wherein said ionophore is a derivative of a 3-oxapentandiaminde-type calcium ionophore, said derivative comprising a polymerizable moiety, wherein said derivative has the structure:

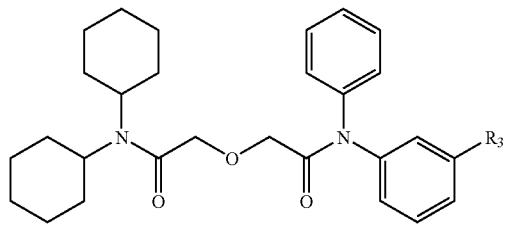

wherein $R_3$ is a substituent comprising an unsaturated group.

22. The ion-detecting sensor of claim 21, wherein $R_3$ is —O(C=O)CH=CH$_2$.

23. The ion-detecting sensor of claim 22, wherein the amount of said ionophore in said polymer is between about 1% and 5% by weight.

24. The ion-detecting sensor of claim 22, wherein the amount of said ionophore in said polymer is about 5% by weight.

25. The ion-detecting sensor of claim 22, wherein said ionophore is selective for calcium ions.

26. An ion-detecting sensor for detecting a target cation in a sample, comprising an ionophore covalently grafted into a self-plasticizing co-polymer, wherein said ionophore is a derivative of a 3-oxapentandiminde-type calcium ionophore having a polymerizable moiety, wherein said ionophore has the structure

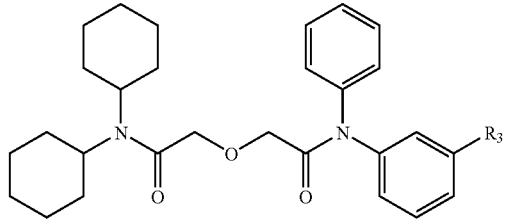

wherein $R_3$ is —O(C=O)CH=CH$_2$.

27. A method of preparing a molecularly imprinted plasticizer-free co-polymer responsive to ions, comprising:
(a) forming a complex between said ions and a functionalized ionophore;
(b) combining said complex with:
(i) methacrylate monomers having $R_1$ or $R_2$ pendant alkyl groups, wherein $R_1$ is any of $C_{1-3}$ alkyl groups and $R_2$ is any of $C_{4-12}$ alkyl groups;
(ii) a cross-linking monomer; and
(iii) a polymerization initiator under conditions that allow said methacrylate monomers to copolymerize and said ionophore to become covalently bonded to said monomers to form a co-polymer containing said ionophore and said ion; and
(c) removing said ions from said polymer to provide said imprinted co-polymer, wherein the co-polymer has a glass transitional temperature ($T_g$) of about or below 0° C.

28. The method of claim 27, wherein said conditions allow said ionophore to copolymerize with said methacrylate monomers.

29. The method of claim 28, further comprising mixing said particles with PVC and a solvent to form a polymer membrane solution.

30. The method of claim 27, wherein said imprinted co-polymer is in the form of particles.

31. The method of claim 27, wherein $R_1$ is any of $C_{1-2}$ alkyl groups and $R_2$ is any of $C_{8-12}$ alkyl groups.

32. The method of claim 27, wherein said functionalized ionophore has the structure:

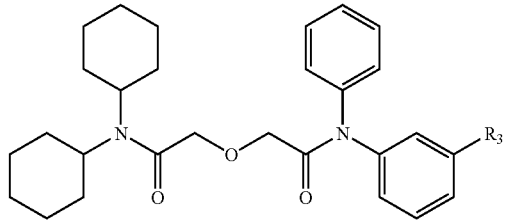

wherein $R_3$ is a substituent comprising an unsaturated group.

33. The method of claim 32, wherein $R_3$ is —O(C=O)CH=CH$_2$.

34. The method of claim 27, wherein in step (a) said ionophore is complexed with magnesium ions and said co-polymer is responsive to magnesium ions.

35. The method of claim 27, wherein in step (a) said ionophore is complexed with calcium ions and said co-polymer is responsive to calcium ions.

36. The method of claim 27, wherein the relative proportion of said cross-linker relative to said copolymer is about 40% on a weight basis.

37. The method of claim 27, wherein said cross-linker is ethylene glycol dimethacrylate.

38. The ion-detecting sensor of claim 37, wherein the ion exchanger is a salt of a halogenated carborane anion.

39. The ion-detecting sensor of claim 38, wherein the halogenated carborane anion is 2, 3, 4, 5, 6, 7, 8, 9, 10, 11, 12 undecabromocarborane, undecachlorinatedcarborane, hexabrominatedcarborane and undecaiodinatedcarborane.

40. The ion-detecting sensor of claim 39, wherein the ion exchanger is trimethylammonium undecaiodinatedcarborane.

41. The method of claim 27, further comprising adding an ion exchanger in step (b).

42. A molecularly imprinted co-polymer prepared by the method of claim 27.

43. A sensor comprising a co-polymer prepared by the method of claim 27, wherein the functionalized ionophore is specific for a target ion.

44. An ionophore having the structure:

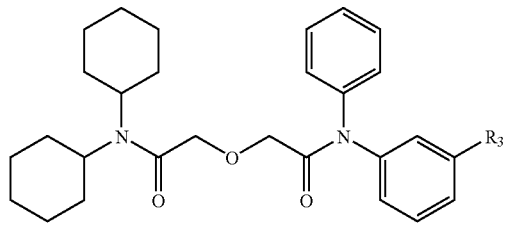

wherein R₃ is a substituent comprising a double bond.

45. The ionophore of claim 44, wherein R₃ is —O(C=O)CH=CH₂.

46. A method of preparing a molecularly imprinted plasticizer-free co-polymer responsive to ions, comprising:
   (a) forming a complex between said ions and a 3-oxapentandiaminde-type calcium ionophore;
   (b) combining said complex with:
      (i) acrylate and/or methacrylate monomers;
      (ii) "a cross-linking monomer; and
      (iii) a polymerization initiator under conditions that allow co-polymerization of said acrylate and/or methacrylate monomers with said ionophore to form a co-polymer containing said ions; and
   (c) removing said ions from said polymer to provide said imprinted co-polymer, wherein said ionophore has the structure:

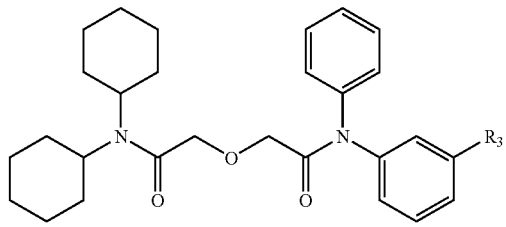

wherein R₃ is a substituent comprising an unsaturated group.

47. The method of claim 46, wherein said ions are magnesium ions.

48. A graft copolymer having selectivity for a target ion, comprising (i) a copolymer comprising polymerized units of methacrylate monomers; and (ii) a functionalized ionophore of said ion, wherein at least a portion of the functionalized ionophore is grafted onto the copolymer through covalent linkages, wherein said ionophore has the structure:

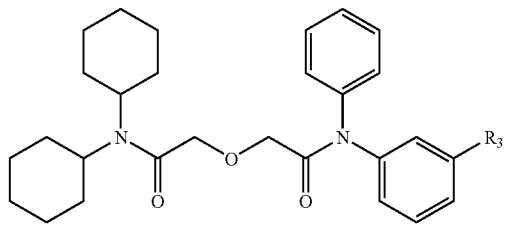

wherein R₃ is a substituent comprising an unsaturated group.

* * * * *